US008552167B2

(12) United States Patent
Chang et al.

(10) Patent No.: US 8,552,167 B2
(45) Date of Patent: Oct. 8, 2013

(54) MULTIFUNCTIONAL APTAMER-NUCLEIC ACID NANOSTRUCTURES FOR TUMOR-TARGETED KILLING

(75) Inventors: Yung Chang, Tempe, AZ (US); Hao Yan, Chandler, AZ (US)

(73) Assignee: Arizona Board of Regents, a body corporate of the State of Arizona Acting for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/392,735

(22) PCT Filed: Oct. 7, 2010

(86) PCT No.: PCT/US2010/051751
§ 371 (c)(1),
(2), (4) Date: Apr. 10, 2012

(87) PCT Pub. No.: WO2011/049750
PCT Pub. Date: Apr. 28, 2011

(65) Prior Publication Data
US 2012/0190732 A1 Jul. 26, 2012

Related U.S. Application Data

(60) Provisional application No. 61/253,389, filed on Oct. 20, 2009.

(51) Int. Cl.
*C07H 21/04* (2006.01)
*A61K 48/00* (2006.01)

(52) U.S. Cl.
USPC ........................................ 536/23.1; 514/44 R

(58) Field of Classification Search
USPC ........................................ 536/23.1; 514/44 R
See application file for complete search history.

(56) References Cited

U.S. PATENT DOCUMENTS 6,255,469 B1 7/2001 Seeman et al.
2004/0249130 A1* 12/2004 Stanton et al. ................ 530/350

FOREIGN PATENT DOCUMENTS

| JP | 2006211905 A | * | 8/2006 |
| WO | 97/41142 A1 | | 11/1997 |
| WO | 2004/047742 A2 | | 6/2004 |
| WO | 2005/001048 A2 | | 1/2005 |
| WO | 2005/111238 A2 | | 11/2005 |
| WO | WO 2005111238 A2 | * | 11/2005 |
| WO | 2006/124089 A1 | | 11/2006 |
| WO | 2008/033848 A2 | | 3/2008 |

OTHER PUBLICATIONS

Translation of JP 2006/211905A, Nakamura et al. (2006), pp. 1-13.*
Seeman, Nadrian C., "Nucleic Acid Junctions and Lattices," J. Theor. Biol., 1982, pp. 237-247, vol. 99.
Green, Maurice, et al., "Autonomous Functional Domains of Chemically Synthesized Human Immunodeficiency Virus Tat Trans-Activator Protein," Cell, Dec. 23, 1988, pp. 1179-1188, vol. 55.
Frankel, Alan D., et al., "Cellular Uptake of the Tat Protein from Human Immunodeficiency Virus," Cell, Dec. 23, 1988, pp. 1189-1193, vol. 55.
Fu, Tsu-Ju, et al., "DNA Double-Crossover Molecules," Biochemistry, 1993, pp. 3211-3220, vol. 32., No. 13.
Fawell, Stephen, et al., "Tat-mediated delivery of heterologous proteins into cells," PNAS, Cell Biology, Jan. 1994, pp. 664-668, vol. 91.
Winfree, Erik, et al., "Design and self-assembly of two-dimensional DNA crystals," Nature, Aug. 6, 1988, pp. 539-544, vol. 394.
Storhoff, James J., et al., "Programmed Materials Synthesis with DNA," Chem. Rev., 1999, pp. 1849-1862, vol. 99, No. 7.
Schwarze, Steven R., et al., "In Vivo Protein Transduction: Delivery of a Biologically Active Protein into the Mouse," Science, Sep. 3, 1999, pp. 1569-1572, vol. 285.
Lee, Sug Hyung, et al., "Alterations of the DR5/TRAIL Receptor 2 Gene in Non-Small Cell Lung Cancers," Cancer Res., Nov. 15, 1999, pp. 5683-5686, vol. 59.
Ho, Alan, et al., "Synthetic Protein Transduction Domains: Enhanced Transduction Potential in Vitro and in Vivo," Cancer Res, Jan. 15, 2001, pp. 474-477, vol. 61.
Tyagi, Mudit, et al., "Internalization of HIV-1 Tat Requires Cell Surface Heparan Sulfate Proteoglycans," J. Biol. Chem., Feb. 2, 2001, pp. 3254-3261, vol. 276, No. 5.
Franco, Agustin V., et al., "The Role of NF-kB in TNF-Related Apoptosis-Inducing Ligand (TRAIL)-Induced Apoptosis of Melanoma Cells," J. Immunol., 2001, pp. 5337-5345, vol. 166.
Seeman, Nadrian C., "DNA in a material world," Nature, Jan. 23, 2003, pp. 427-431, vol. 421.
Yan, Hao, et al., "Directed nucleation assembly of DNA tile complexes for barcode-patterned lattices," PNAS, Jul. 8, 2003, pp. 8103-8108, vol. 100, No. 4.
Yan, Hao, et al., "DNA-Templated Self-Assembly of Protein Arrays and Highly Conductive Nanowires," Science, Sep. 26, 2003, pp. 1882-1884, vol. 301.
Seeman, Nadrian C., "At the Crossroads of Chemistry, Biology, and Materials: Structural DNA Nanotechnology," Chem. Biol., Dec. 2003, pp. 1151-1159, vol. 10.
Zheng, Shi-Jun, et al., "Critical roles of Trail in hepatic cell death and hepatic inflammation," J. Clin. Invest., Jan. 2004, pp. 58-64, vol. 113, No. 1.
Dechant, Markus J., et al., "Mutation Analysis of the Apoptotic 'Death Receptors' and the Adaptors TRADD and FADD/MORT-1 in Osteosarcoma Tumor Samples and Osteosarcoma Cell Lines," Int. J. Cancer, 2004, pp. 661-667, vol. 109.
Ohuchi, Shoji P., et al., "Selection of RNA aptamers against recombinant transforming growth factor-β type III receptor displayed on cell surface," Biochimie, Mar. 2006, pp. 897-904, vol. 88.
Shangguan, Dihua, et al., "Aptamers evolved from live cells as effective molecular probes for cancer study," PNAS, Aug. 8, 2006, pp. 11838-11843, vol. 103, No. 32.

(Continued)

Primary Examiner — J. E. Angell
(74) Attorney, Agent, or Firm — McDonnell Boehnen Hulbert & Berghoff LLP

(57) ABSTRACT

The present invention provides compositions comprising a ligand-nucleic acid nanostructure that promote tumor cell-specific killing and methods of using the compositions. Specially, the invention provides aptamer-nucleic acid nanostructures for treating tumors in a mammal. The methods of making the compositions are also provided.

24 Claims, 7 Drawing Sheets

(56) References Cited

OTHER PUBLICATIONS

Drosopoulos, K. et al., "Multifaceted Targeting in Cancer: The Recent Cell Death Players Meet the Usual Oncogene Suspects," Expert Opin. Ther. Targets, May 2007, pp. 641-659, vol. 11, No. 5.

Tang, Zhiwen, et al., "Selection of Aptamers for Molecular Recognition and Characterization of Cancer Cells," Anal. Chem., Jul. 1, 2007, pp. 4900-4907, vol. 79, No. 13.

McNamara, James O., et al., "Multivalent 4-1BB binding aptamers costimulate CD8+ T cells and inhibit tumor growth in mice," J. Clin. Invest., Jan. 2008, pp. 376-386, vol. 118, No. 1.

Shaman, Steven M., et al., "Complex Target SELEX," Acc. Chem. Res., Jan. 2008, pp. 130-138, vol. 41, No. 1.

Ke, Yonggang, et al., "Self-Assembled Water-Soluble Nucleic Acid Probe Tiles for Label-Free RNA Hybridization Assays," Science, Jan. 11, 2008, pp. 180-183, vol. 319.

Peek, Laura J., et al., "Nanotechnology in vaccine delivery," Adv. Drug. Deliv. Rev., Feb. 7, 2008, pp. 915-928, vol. 60.

Hasegawa, Hijiri, et al., "Improvement of Aptamer Affinity by Dimerization," Sensors, Feb. 19, 2008, pp. 1090-1098, vol. 8.

Jabr-Milane, Lara, et al., "Multi-functional nanocarriers for targeted delivery of drugs and genes," J. Control. Rel., Apr. 29, 2008, pp. 121-128, vol. 130.

Phillips, Joseph A., et al., "Applications of aptamers in cancer cell biology," Anal. Chim. Acta, May 21, 2008, pp. 101-108, vol. 621.

Keefe, Anthony D., et al., "SELEX with modified nucleotides," Curr. Opin. Chem. Biol., Jul. 21, 2008, pp. 448-456, vol. 12.

Ashkenazi, A., "Directing Cancer Cells to Self-Destruct with Pro-Apoptitic Receptor Agonists" Nature Reviews on Drug Discovery, Dec. 2008, pp. 1001-1012, vol. 7.

Newsom-Davis, T., et al., "Is TRAIL the Holy Grail of Cancer Therapy?" Apoptosis, Apr. 2009, pp. 607-623, vol. 14, No. 4.

International Search Report and Written Opinion for PCT Application No. PCT/US2010/051751, 11 pages, (Feb. 15, 2011).

International Preliminary Report on Patentability for PCT/US2010/051751, 6 pages, (Feb. 15, 2011).

\* cited by examiner

FIG. 1B

- TRAIL-receptors, also known as death receptors (DR4 and DR5)
- Tumor-specific surface proteins that can be targeted by specific aptamers
- Aptamers binding to TRAIL-receptors
- Aptamers binding to tumor-specific proteins
- Nucleic acid nanostructure to hold both sets of aptamers as well as other biomolecules (e.g., NF-κB inhibitors)

MULTIFUNCTIONAL APTAMER-NUCLEIC ACID NANOSTRUCTURES FOR TUMOR-TARGETED KILLING

CROSS REFERENCE TO RELATED APPLICATION

This application claims priority from U.S. Provisional Application No. 61/253,389 filed Oct. 20, 2009, which is incorporated by reference in its entirety.

The sequence listing submitted herewith is incorporated by reference in its entirety.

FIELD OF THE INVENTION

The present invention relates to the fields of cell biology, tumor biology, nucleic acid-based tiling arrays, nanotechnology, and related fields.

BACKGROUND OF THE INVENTION

Despite decades of research efforts, cancer remains today's most pressing health concerns. Current cancer therapies primarily focus on surgical resection, radiotherapy, and chemotherapy. Radiation therapy and many chemotherapeutic compounds trigger the intrinsic apoptotic pathway by inducing DNA damage and cellular stress, which block DNA replication and inhibit tumor cell division. These conventional therapies, however, often cause systemic toxicity and become ineffective when resistant tumors emerge.

Recently, attention has been focused on a new generation of drugs targeting tumor-related biological molecules, such as Traztuzumab, a monoclonal antibody that targets the human epidermal growth factor receptor (HER-2) in breast cancer. In addition, induction of extrinsic apoptotic pathway has been noted as a promising approach of tumor therapy. Tumor necrosis factor (TNF) and tumor necrosis factor-related apoptosis-inducing ligand (TRAIL or Apo2 ligand) are recently discovered targeted therapeutics. TRAIL is a member of the tumor necrosis factor (TNF) cytokine family that induces apoptosis upon binding to its death domain containing receptors TNF receptor (TNFR), TRAIL receptor 1 (TRAIL-R1, also known as death receptor 4 or DR4) and TRAIL receptor 2 (TRAIL-R2, also known as death receptor 5 or DR5). TRAIL binds to TRAIL-R1 and TRAIL-R2 and triggers TRAIL-induced apoptosis. Upon binding to their respective receptors, TNF and TRAIL trigger trimerization of the death receptors and recruitment of death domain-containing mediator proteins. The cascade of protein activation leads to the activation of the initiator caspase, caspase 8, and subsequently the effector caspases, which act on the death substrate in apoptosis.

So far, five TRAIL receptors have been discovered: two are agonist receptors TRAIL-R1 and TRAIL-R2 and three are antagonistic receptors TRAIL-R3 (also known as decoy receptor 1, DcR1), TRAIL-R4 (DcR2) and osteoprotegerin. DcR1 and DcR2 as decoy membrane receptors can bind to TRAIL, but cannot transmit the apoptotic signal because they do not contain functional intracellular death domains. Osteoprotegerin is a secreted TNF receptor family member and may be a soluble antagonist receptor for TRAIL.

Tumor therapy using purified recombinant TRAIL has entered clinical trials. The prospects of recombinant TRAIL anti-cancer therapy, however, have been dampened by reports of hepatotoxicity and tumor resistance. Although TRAIL preferentially induces apoptosis in cancerous cells than normal cells, not all tumor cells are sensitive to TRAIL. The basis for the resistance may be multifaceted, ranging from the competition of decoy receptors for TRAIL binding to up-regulation of NF-κB, an anti-apoptosis factor induced by TRAIL signaling. Though it has been proposed that combination of recombinant TRAIL therapy with traditional chemotherapy or radiation therapy may overcome TRAIL resistance, the non-selective nature of the conventional therapies may cause damages to normal cells.

TRAIL-R1 and TRAIL-R2 agonistic antibodies have been developed and under clinical trials with the hope that the specificity for death receptors may eliminate tumor resistance resulted from decoy receptor competition. The generation of antibodies or humanized antibodies, however, is time consuming and cumbersome. In addition, tumor resistance caused by death receptor mutations that abolish antibody binding to the receptors has been reported. See Lee et al. 1999, Alterations of the DR5/TRAIL receptor 2 gene in non-small cell lung cancers, *Cancer Research* 59(22):5683-6, and Dechant et al., 2004, Mutation analysis of the apoptotic "death-receptors" and the adaptors TRADD and FADD/MORT-1 in osteosarcoma tumor samples and osteosarcoma cell lines, *Int. J. Cancer* 109:661-667.

Thus, there exists a need in the art for a more effective and adaptable anti-tumor therapy based on the death receptors induced extrinsic apoptosis pathway.

SUMMARY OF THE INVENTION

In one aspect, the present invention provides compositions comprising a first ligand that is specific for binding to a tumor cell, and a second ligand that is specific for binding to a death receptor on the tumor cell, wherein the first and second ligands are bound to a nucleic acid nanostructure. In certain preferred embodiments, the first ligand is a first aptamer, and the second ligand is a second aptamer. In certain preferred embodiments, the first and second aptamers are linked by one or more linker oligonucleotides to form one or more multi-specific aptamers wherein the first and second aptamers are separated by 15-45 nucleotides, more preferably 30-45 nucleotides (or 5-15 nm, more preferably 10-15 nm in spacing) in the multispecific aptamer. In certain preferred embodiments, the first aptamer is specific for binding to a tumor antigen on the surface of the tumor cell. In certain other preferred embodiments, the tumor antigen is CD20 (GenBank Accession No. NM_152866, SEQ ID NO:1, and NP_690605.1, SEQ ID NO:2) for B cell lymphoma, Her2/Neu for breast cancer (NM_001005862, SEQ ID NO:3, and NP_001005862, SEQ ID NO:4), PSMA for prostate cancer (NM_001014986, SEQ ID NO:5, and NP_001014986, SEQ ID NO:6), and Muc1 (NM_002456, SEQ ID NO:7, and NP_002447, SEQ ID NO:8) for many different cancers, including cancers derived from breast, lung, prostate, colon and bladder tissues. In addition, any newly identified tumor-associated antigens can be targeted for the selection of tumor-specific aptamers. In yet other preferred embodiments, the death receptor is TRAIL Receptor 1 (TRAIL-R1) (NM_003844, DNA and protein sequences are shown in SEQ ID NO:9 and SEQ ID NO:10, respectively), TRAIL Receptor 2 (TRAIL-R2) (NM_003842, DNA and protein sequences are shown in SEQ ID NO:11 and SEQ ID NO:12, respectively), Fas (NM_080685, DNA and protein sequences are shown in SEQ ID NO:13 and SEQ ID NO:14, respectively), tumor necrosis factor receptor I (TNFRI or CD120a, NM_001065, DNA and protein sequences are shown in SEQ ID NO:15 and SEQ ID NO:16, respectively), TNFRII (CD120b, NM 001066, DNA and protein sequences are shown in SEQ ID NO:17 and SEQ ID NO:18, respectively), or TNFRIII (LTBR or CD18, NM_002342, DNA and protein sequences are shown in SEQ ID NO:19 and SEQ ID NO:20, respectively). In certain preferred embodiments of this aspect, the distance between the first aptamer and the second aptamer on the nucleic acid nanostructure is about 5 nm to about 15 nm, preferably about 10 nm to about 15 nm.

In further preferred embodiments of this aspect, the first aptamer comprises a plurality of first aptamers, and the second aptamer comprises a plurality of second aptamers. Each aptamer of the plurality of aptamers can bind to the same or different binding sites on the target protein. In certain preferred embodiments, the plurality of first aptamers is present on the nucleic acid nanostructure at a density of 5-10 aptamers per nucleic acid nanostructure, and the plurality of second aptamers is present on the nucleic acid nanostructure at a density of 5-10 aptamers per nucleic acid nanostructure. In certain other preferred embodiments, the distance between each aptamer of the plurality of first aptamers and the distance between each aptamer of the plurality of second aptamers on the nucleic acid nanostructure is about 5 nm to about 15 nm, and more preferably, 5-8 nm. In certain preferred embodiments, the distribution of the first and second aptamers on the nucleic acid nanostructure is not uniform. In certain preferred embodiments, the distance between two of the first aptamers of the plurality of the first aptamers and/or the distance between two of the second aptamers of the plurality of the second aptamers is about 5-8 nm in some portions, and the distance is about 8-10 nm in other portions, of the nucleic acid nanostructure. In certain other preferred embodiments, the distance between a first aptamer and a second aptamer is from about 10 to about 12 nm in some portions, and the distance is from about 13 to about 15 nm in other portions, of the nucleic acid nanostructure. The spacing can be varied depending on the distribution or density of the target molecules on the surface of the cells. Methods for determining the distribution or density of a target molecule on the cell surface are within the knowledge of one of ordinary skill in the art, including without limitation immuno-fluorescence staining and flow cytometry, wherein stronger surface fluorescence staining indicates higher density of the target molecule on the cell surface. In certain preferred embodiments, the ratio of first aptamers to second aptamers on the nucleic acid nanostructure is 1:1.

In certain preferred embodiments of this aspect, the first aptamer comprises a dimer, trimer, tetramer, or pentamer of an aptamer that is specific for a tumor cell. In certain other preferred embodiments, the second aptamer comprises a dimer, trimer, tetramer, or pentamer of an aptamer that is specific for binding to the death receptor. In other preferred embodiments, the first aptamer comprises a plurality of first aptamers, and/or the second aptamer comprises a plurality of second aptamers. In certain preferred embodiments, the plurality of first aptamers is present on the nucleic acid nanostructure at a density of 5-10 aptamers per nucleic acid nanostructure, and the plurality of second aptamers is present on the nucleic acid nanostructure at a density of 5-10 aptamers per nucleic acid nanostructure. In yet other preferred embodiments, the distance between each aptamer of the plurality of first aptamers and the distance between each aptamer of the plurality of second aptamers on the nucleic acid nanostructure is about 10 nm to about 15 nm. And in certain particular preferred embodiments, the ratio of first aptamers to second aptamers on the nucleic acid nanostructure is 1:1. Further, in certain preferred embodiments, the first aptamer comprises a plurality of first aptamers that is specific for binding to at least two different tumor antigens on the surface of the tumor cell; in certain other preferred embodiments, the second aptamer comprises a plurality of second aptamers that is specific for binding to at least two different death receptors on the tumor cell.

In other preferred embodiments of this invention, the composition further comprises one or more apoptosis inducers that are bound to the nucleic acid nanostructure. Suitable apoptosis inducers include without limitation an siRNA molecule, an antisense oligonucleotide or a decoy oligonucleotide against anti-apoptosis proteins including without limitation NF-κB (NM_003998.3, DNA and protein sequences are shown in SEQ ID NO:21 and SEQ ID NO:22, respectively), STAT 3 (NM_139276, DNA and protein sequences are shown in SEQ ID NO:23 and SEQ ID NO:24, respectively), survivin (NM_001168, DNA and protein sequences are shown in SEQ ID NO:25 and SEQ ID NO:26, respectively), bcl-2 (NM_000633, DNA and protein sequences are shown in SEQ ID NO:27 and SEQ ID NO:28, respectively), and cFLIP (NM_001127183, DNA and protein sequences are shown in SEQ ID NO:29 and SEQ ID NO:30, respectively).

Exemplary siRNA sequences for NF-κB and STAT 3 include without limitation 5'-AGU CCA GGA UUA UAG CCC CdTdT for NF-κB (SEQ ID NO:31) and 5'-AAC AUC UGC CUA GAU CGG CUA dTdT-3' for STAT 3 (SEQ ID NO:32).

In certain preferred embodiments, the apoptosis inducer is an NF-κB inhibitor. In certain other preferred embodiments, the NF-κB inhibitor is a decoy oligonucleotide having the sequence 5'-GGATTTCCC-3'. In certain other preferred embodiments, the apoptosis inducer is a STAT3 inhibitor; in yet other preferred embodiments, the STAT3 inhibitor is a STAT3 decoy oligonucleotide having the sequence 5'-CATTTCCCGTAAATC-3' as identified by SEQ ID NO:33.

In certain preferred embodiments, the nucleic acid nanostructure comprises 4-10 copies of one type of apoptosis inducer; while in other preferred embodiments, the nucleic acid nanostructure comprises 4-10 copies of each of more than one type of apoptosis inducers. In certain preferred embodiments, the nucleic acid nanostructure comprises both NF-kB decoy oligonucleotides and STAT 3 decoy oligonucleotides at a ratio of 1:1.

In certain further preferred embodiments, the nucleic acid nanostructure comprises a nucleic acid tile. In certain preferred embodiments, the nucleic acid nanostructure comprises a plurality of nucleic acid tiles; in certain other preferred embodiments, the plurality of nucleic acid tiles forms a nucleic acid tiling array. In certain particular preferred embodiments, the aptamer-nucleic acid nanostructure is between about 10 nm and about 2000 nm in length. In certain preferred embodiments, the aptamer-nucleic acid nanostructure is 100 nm in length; while in other preferred embodiments, the aptamer-nucleic acid nanostructure is 100-2000 nm in length. In certain other preferred embodiments, the composition of this aspect of the invention further comprises a pharmaceutically acceptable carrier.

In another aspect, the invention provides methods of treating a tumor in a mammal comprising administering to a mammal in need thereof an amount effective to treat the tumor of a composition that comprises a first ligand that is specific for a tumor cell, and a second ligand that is specific for a death receptor on the tumor cell, wherein the first and second ligands are bound to a nucleic acid nanostructure. In certain preferred embodiments, the first ligand is a first aptamer and the second ligand is a second aptamer. In certain other preferred embodiments, the tumor cell is selected from the group consisting of lymphoma cell, breast cancer cell, melanoma cell, plasmacytoma cell, sarcoma cell, glioma cell, thymoma cell, leukemia cell, prostate cancer cell, colon cancer cell, esophageal cancer cell, lung cancer cell, ovarian cancer cell, cervical cancer cell, hepatoma cell, and gastric cancer cell. In certain other preferred embodiments, the invention provides methods of treating a tumor in a mammal comprising administering to a mammal in need thereof an amount effective to treat the tumor a composition according to any embodiments of the first aspect of the invention.

In yet another aspect, the invention provides methods of making the composition of the first aspect, comprising contacting a first aptamer, a second aptamer, and at least one polynucleotide under conditions suitable for binding of the first and second aptamers to the at least one polynucleotide to form an aptamer-nucleic acid nanostructure, wherein the first aptamer is specific for a tumor cell and the second aptamer is specific for binding to a death receptor on the tumor cell. In certain preferred embodiments, the at least one polynucleotide comprises a plurality of polynucleotides, and wherein the contacting is done under conditions suitable to promote hybridization of the plurality of polynucleotides into at least one nucleic acid tile. In certain other preferred embodiments, the at least one nucleic acid tile comprises a plurality of nucleic acid tiles, and wherein the plurality of nucleic acid tiles forms at least one nucleic acid tiling array.

Specific embodiments of the present invention will become evident from the following more detailed description of certain preferred embodiments and the claims.

DETAILED DESCRIPTION OF THE INVENTION

Figure 1A:
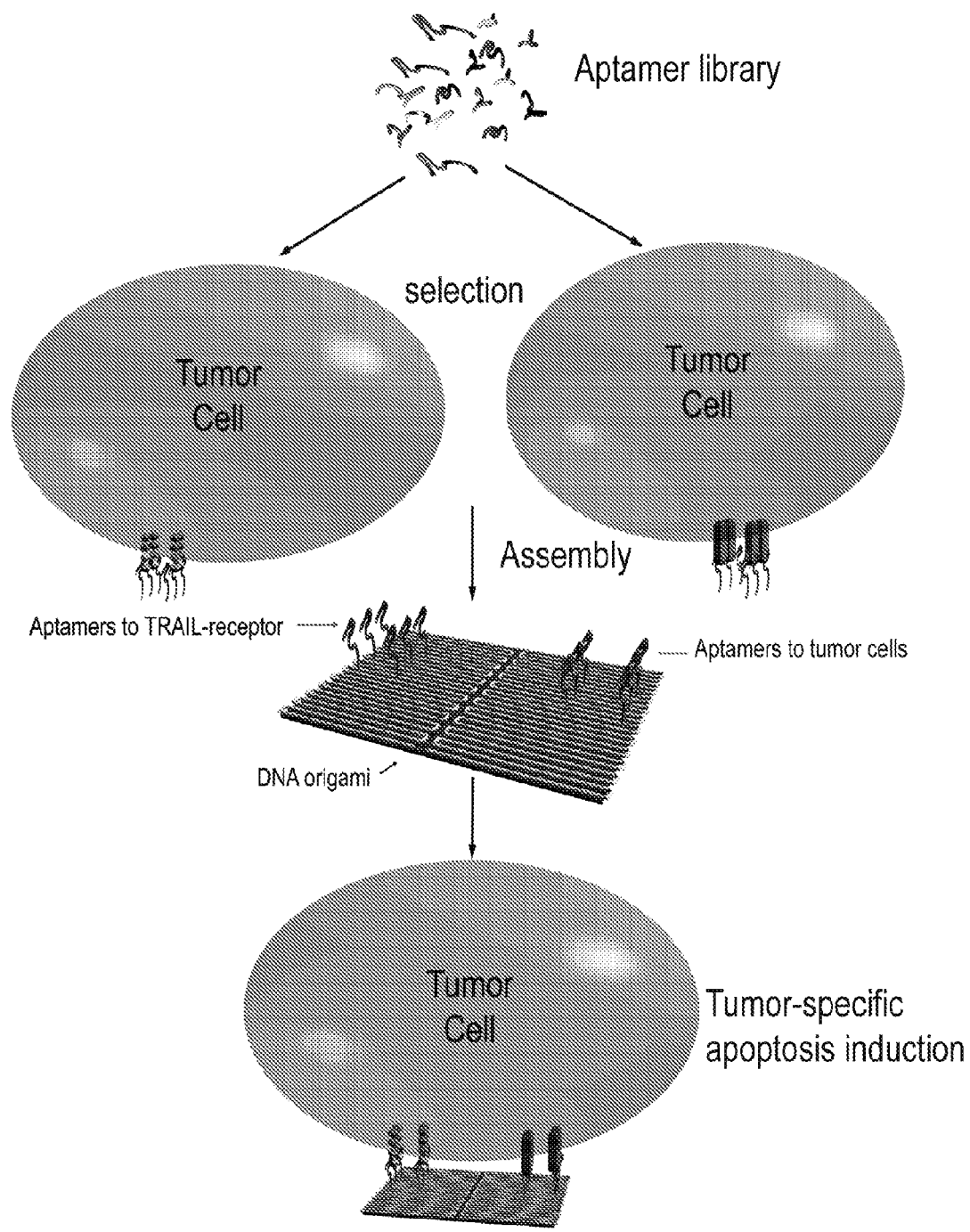
FIG. 1 shows a diagram illustrating the structure and function of an exemplary aptamer-nucleic acid nanostructure for tumor-specific induction of apoptosis where the nucleic acid nanostructure is represented by a DNA tile or tiling array.
Figure 2:
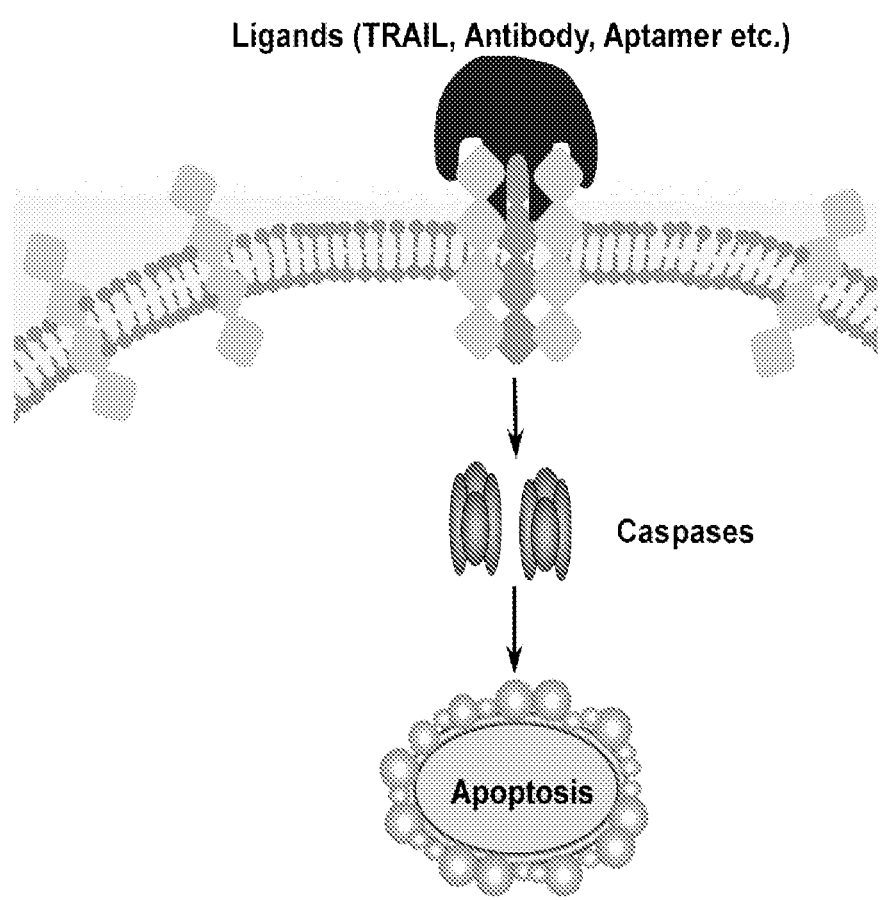
FIG. 2 shows a diagram illustrating apoptosis induction induced by the engagement of TRAIL-receptors by TRAIL-receptor agonists, such as TRAIL, antibodies or aptamers, the engagement of which causes cross-linking of the TRAIL-receptors.

All publications, patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press) and *PCR Protocols: A Guide to Methods and Applications* (Innis, et al. 1990. Academic Press, San Diego, Calif.).

As used herein, the singular forms "a", "an" and "the" include plural referents unless the context clearly dictates otherwise. For example, reference to a "nucleic acid" means one or more nucleic acids.

As used herein, the terms "polynucleotide", "nucleotide", "oligonucleotide", and "nucleic acid" may be used interchangeably to refer to nucleic acid comprising DNA, RNA, derivative thereof, or combination thereof.

As used herein, "nucleic acid" means DNA, RNA, peptide nucleic acids ("PNA"), and locked nucleic acids ("LNA"), nucleic acid-like structures, as well as combinations thereof and analogues thereof, unless specifically indicated. Nucleic acid analogues include known analogues of natural nucleotides which have similar or improved binding properties. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

As used herein, the term "binding to" or "bound to" refers to any of direct binding, indirect binding, covalent binding, or non-covalent binding, unless otherwise specifically indicated.

As used herein, the term "ligand" is any molecule capable of binding to a target. Such ligands include, but are not limited to, proteins, lipids, carbohydrates, nucleic acids (including, but not limited to, aptamers), and other molecules. In certain preferred embodiments, the ligand refers to a binding partner that binds to a cell surface molecule or receptor. In certain preferred embodiments of the invention, the ligand is a monovalent ligand; in other preferred embodiments, the ligand is a multivalent ligand, which can be without limitation a homomultimeric or heteromultimeric ligand. In certain other preferred embodiments, a ligand is an aptamer or an agonistic antibody.

In a first aspect, the invention provides compositions comprising a first ligand that is specific for binding to a tumor cell, and a second ligand that is specific for binding to a death receptor on the tumor cell, wherein the first and second ligands are bound to a nucleic acid nanostructure. In certain preferred embodiments, the first ligand is a first aptamer and the second ligand is a second aptamer. In certain preferred embodiments, the first aptamer binds to a tumor antigen on the surface of a tumor cell.

As used herein, the term "specific binding" of "specific for binding" to a target molecule is used consistently with the term used in the art of immunology and ligand/receptor interaction in general. For example, a second aptamer specific for binding to a death receptor on the tumor cell indicates that the second aptamer specifically binds to a target death receptor under stringent binding conditions and that the aptamer's binding, if any, to other non-target death receptor or other molecules that do not have the same binding site under the same binding conditions is insubstantial or undetectable as determined by methods commonly used in the immunology or ligand/receptor art. Stringent binding conditions can be determined by one of ordinary skill in the art further aided by the disclosure of the instant application and knowledge known in the art. See Sambrook et al. supra. Specific binding can also be determined by competition; for example, a specific binding between a labeled ligand and its receptor under stringent binding conditions can be competed by the unlabeled ligand, but not by other unlabeled irrelevant molecules that are present at equal molar concentration with the labeled ligand.

As used herein the term "tumor antigen" refers to a molecule that is present on a tumor cell, especially on the surface of a tumor cell, and not present to a detectable level on the corresponding non-tumor or normal cell. Alternatively, the term "tumor antigen" refers to a molecule that is present in at least a 10-fold higher level on the surface of a tumor cell than on the corresponding non-tumor or normal cell. Thus, the tumor antigen offers tumor-specific recognition. Known tumor antigens suitable for use in the instant application to provide tumor-specific targeting include without limitation CD20 for B cell lymphoma, Her2/neu (human epidermal growth receptor 2) for breast cancer, PSMA (prostate-specific membrane antigen) for prostate cancer, Muc1 (mucin 1) for many different cancers, including cancers derived from breast, lung, prostate, colon and bladder tissues. Tumor antigens are not limited to protein or peptide molecules; any molecule, such as lipid or carbohydrate that is present predominantly on tumor cells verses normal cells is suitable for use as a tumor antigen in the instant invention. In advantageous embodiments, tumor-specific targeting by the binding of the first aptamer to a tumor antigen greatly reduces non-specific cell killing and cytotoxicity that is currently encountered in existing TRAIL-centered anti-cancer therapies.

The present invention also provides methods for identifying previously unknown tumor antigens. An aptamer that binds to a tumor cell but not to a corresponding normal or non-tumor cell recognizes a tumor antigen on the surface of the tumor cell. The molecule on the tumor cell surface bound by the aptamer can be purified by methods known in the art, such as affinity purification and the identity of the molecule can be analyzed. However, the identity of the tumor antigen is not necessary for using the tumor antigen in the instant application: a cell surface molecule that is present on the tumor cell but not on the corresponding non-tumor or normal cell offers tumor-specific targeting.

As used herein the term "death receptor" refers to a receptor to a ligand belonging to the tumor necrosis factor family. Tumor necrosis factor (TNF) family refers to a group of cytokines, including TNF-α (NM_000594, DNA and protein sequences are shown in SEQ ID NO:34 and SEQ ID NO:35, respectively), TNF-β (NM_000595, DNA and protein sequences are shown in SEQ ID NO:36 and SEQ ID NO:37, respectively), TRAIL (NM_003810, DNA and protein sequences are shown in SEQ ID NO:38 and SEQ ID NO:39, respectively), and FAS ligand (NM_000639, DNA and protein sequences are shown in SEQ ID NO:40 and SEQ ID NO:41, respectively), which binds to its respective receptor and can cause cell death. A death receptor contains one or more functional death domains. Newly discovered death receptors can be identified by the presence of signature TNFR domains, which consist of three tandem repeats of cysteine-rich domains (CRDs). The binding of a ligand, an agonistic antibody or aptamer to a death receptor triggers oligomerization of the death receptor and death domain-induced activation of caspases and cell death. In certain preferred embodiments, the death receptors include without limitation TNFRI, TNFRII, TNFRIII, FAS, TRAIL-R1, and TRAIL-R2.

The term "aptamer" as used herein refers to single-stranded nucleic acid molecules with secondary structures that facilitate high-affinity binding to a target molecule. In certain preferred embodiments, the single-stranded nucleic acid is ssDNA, RNA or derivatives thereof. The aptamer comprises nucleic acid sequence that does not participate in base-pairing with other polynucleotides within the nucleic acid nanostructure.

Aptamers can be synthesized and screened by any suitable methods in the art. For example, aptamers can be screened and identified from a random aptamer library by SELEX (systematic evolution of ligands by exponential enrichment). In certain preferred embodiments, aptamers that bind to a cell surface target molecule can be suitably screened and selected by a modified selection method herein referred to as cell-SELEX or cellular-SELEX, even if the identity of the cell surface target molecule is unknown (Phillips et al., 2008, *Anal Chim Acta* 621:101-108; Shamah et al., 2008, *Acc Chem Res* 41:130-138). In certain other preferred embodiments, aptamers that bind to a cell surface target molecule can be screened by capillary electrophoresis and enriched by SELEX based on the observation that aptamer-target molecule complexes exhibited retarded migration rate in native polyacrylamide gel electrophoresis as compared to unbound aptamers.

In certain preferred embodiments, a random aptamer library can be created that contains monomeric, dimeric, trimeric, tetrameric or other higher multimeric aptamers. A random aptamer library (either ssDNA or RNA) can be modified by including oligonucleotide linkers to link individual aptamer monomers to form multimeric aptamer fusion molecules. In certain preferred embodiments, a random oligonucleotide library is synthesized with randomized 45 nt sequences flanked by defined 20 nt sequences both upstream and downstream of the random sequence, i.e., known as 5'-arm and 3'-arm, which are used for the amplification of selected aptamers. A linking oligonucleotide (i.e., linker) is designed to contain sequences complementary to both 5'-arm and 3'-arm regions of random aptamers to form dimeric aptamers. For trimeric or tetrameric aptamers, a small trimeric or tetrameric (i.e., a Holiday junction-like) DNA nanostructure will be engineered to include sequences complementary to the 3'-arm region of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors. Alternatively, multimeric aptamers can also be formed by mixing biotinylated aptamers with streptavidin.

A modified cellular SELEX procedure can be employed to select target-binding aptamers. Multimeric aptamers may have multivalent but single binding specificity, or multivalent and multi-specific binding activity. Both types of these aptamer molecules are desirable as long as they display high binding avidity to target cells. For example, if aptamers with multiple specificities are selected by cellular binding, their corresponding cellular receptors likely reside in close vicinity on the cell surface or are different binding sties of one surface molecule. These types of aptamers are most likely present in the initial random library or during the early stage of cellular SELEX selection. If the multi-specific aptamers can survive rounds of selection, they may have advantage of targeting several co-receptors and therefore triggering multiple signaling pathways for cellular activation. On the other hand, multivalent but single target-binding aptamers are expected to be more readily selected by the cellular SELEX because of their intrinsic high binding avidity. This type of aptamer molecules can be used to target both tumor cells and effector cells.

In certain other preferred embodiments, for the selection of target specific RNA-aptamers, a well-established RNA-aptamer selection protocol (Ohuchi et al., 2006. *Biochimie* 88:897-904) is applied with some modification. The dsDNA after PCR amplification of the random DNA library is transcribed to generate a RNA pool using T7-RNA polymerase. This RNA library is optionally incubated with linkers to form multivalent aptamer library. The aptamers from the library are incubated with target tumor cells and counter-selected against normal cells or other non-target tumor cells. The selected RNA aptamers are reversely transcribed into cDNA and amplified by PCR, which will then be transcribed into RNA. These RNA molecules can be incubated with linkers to form multivalent aptamers for the next round of selection and amplification. Aptamers of ssDNA or RNA aptamers labeled with fluorophore can be used to reveal aptamer-specific cell binding by flow cytometry. Furthermore, the aptamers specific for a tumor antigen or death receptor can also be enriched through FACS-based cell sorting. After 20-30 cycles of positive/negative selection, the selected aptamers can be cloned and sequenced. The binding valence and specificity of selected multimeric aptamer can be further characterized. For example, the binding aptamers can be eluted from the cells and analyzed by gel electrophoresis for the size and species, some of which will be analyzed by sequence analyses.

Aptamers are known as "chemical antibodies" in that it shares the specificity of antibodies but enjoys the advantages of adaptability. Development of antibodies is a process that takes time. A random sequence aptamer library, on the other hand, can be efficiently synthesized and screened for suitable binders to a target molecule with desirable affinity. One of the concerns over TRAIL-R agonist antibody-based therapy is the emerging of resistant tumors caused by the occurrence of mutations in the TRAIL-R proteins that abolish antibody binding. In the aptamer-based therapy, on the other hand, new aptamers that are capable of specific binding to the mutant TRAIL-Rs can be quickly screened and identified. Such aptamers can be used to overcome tumor resistance.

Further, humanized antibody is preferred for administering to a human subject. The development and production of a suitable humanized TRAIL-R antibody is a time consuming and cumbersome process. As compared to antibodies developed in non-human animals, aptamers are immunogenically inert. Thus, in certain advantageous embodiments, the invention provides aptamer-nucleic acid nanostructure that induces minimal or no immune response when administered into a human subject.

In certain preferred embodiments, a suitable nucleotide length for an aptamer ranges from about 25 to about 100 nucleotide (nt), and in various other preferred embodiments, 30-100 nt, 30-60 nt, 25-70 nt, 25-60 nt, 40-60 nt, or 40-70 nt in length. In certain preferred embodiments, the length of an aptamer is about 2-20 nm, in various other preferred embodiments, 2-15 nm, 5-15 nm, 5-10 nm, or less than 10 nm in size. In certain preferred embodiments, the monomeric aptamer contains a predetermined sequence that is about 8-10 nm in length (25-30 nt in length). However, the sequence can be designed with sufficient flexibility such that it can accommodate interactions of aptamers with two targets at the distances described herein.

Individual aptamers generally have lower binding affinity than antibodies. In certain preferred embodiments, the aptamer has affinity at the range of 10-100 nM, which, after binding of the aptamer to a tumor cell surface molecule, permits dissociation of the aptamer from the target molecule, which leads to the release and recycle of the aptamer nucleic acid nanostructure to target other tumor cells. In certain other preferred embodiments, the affinity of individual aptamers can be increased by 4-50 fold by constructing multimeric aptamers linked together by covalent or non-covalent linkages. Thus, in certain preferred embodiments, the desirable affinity of an aptamer to a target death receptor can be fine-tuned by adjusting the multiplexity of the monomeric aptamer binding units on the nucleic acid nanostructure.

In certain embodiment of this aspect of the invention, the composition comprises multimeric first and/or second aptamers. As used herein, the term "multimeric aptamer" or "multivalent aptamer" refers to an aptamer that comprises multiple monomeric binding units, wherein each of the monomeric binding unit can be an aptamer on its own. Similarly, in certain preferred embodiments of this aspect, the first aptamer comprises a dimer, trimer, tetramer, or pentamer of an aptamer or a monomeric binding unit, wherein the first aptamer is capable of binding to one or more cell surface proteins of a tumor cell, and/or the second aptamers comprises a dimer, trimer, tetramer, or pentamer of an aptamer or a monomeric binding unit wherein the second aptamer is capable of binding to one or more death receptors.

A multimeric aptamer can be a homomultimer or a heteromultimer. The term "homomultimer" refers to a multimeric aptamer that comprises multiple binding units of the same kind, i.e., each binding unit binds to the same binding site of the same target molecule. The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sties or a multimeric aptamer that binds to different target molecules. A heteromultimer that binds to different target molecules can also be referred to as a multi-specific multimer. In certain preferred embodiments, the invention provides compositions that comprise multi-specific multimeric first aptamers that bind to different tumor antigens on the tumor cell and/or multi-specific multimeric second aptamers that bind to different death receptors on the tumor cells. In certain preferred embodiments. the multi-specific multimeric second aptamers bind to TRAIL-R1 and TRAIL-R2 on the tumor cell.

Multimeric aptamers with monomeric binding units that each bind to the same target molecule acquire higher binding avidity than their monomeric counterparts and therefore are likely to be preferentially selected by cellular SELEX. On the other hand, multimeric aptamers with monomeric binding units that each bind to different target molecules may also possess binding advantages if two or three aptamer binding motifs happen to interact with their ligands located at close vicinity on the cell surface. Interactions among these different receptor/ligand pairs can also synergize the binding activity as well. Multimers of aptamer binding unit can be covalently linked to each other. Alternatively, multimers of aptamer binding units can be linked to each other by direct base pairing with each other or with a linker polynucleotide, or other non-covalent linkage including without limitation, biotin-streptavidin interaction. Multimeric aptamers provide multivalent binding capacity either for one type of target molecule or receptor, or for multiple types of target molecules or receptors.

In certain preferred embodiments, the linker polynucleotide has a length between about 5 nucleotides (nt) and about 100 nt; in various other preferred embodiments, 10-30 nt, 20-30 nt, 25-35 nt, 30-50 nt, 40-50 nt, 50-60 nt, 55-65 nt, 50-80 nt, or 80-100 nt. It is within the ability of one of skill in the art to adjust the length of the linker polynucleotide to accommodate each monomeric ligand present on the nucleic acid nanostructure.

In certain preferred embodiments, the multimeric aptamers can be identified and screened from a random multimeric aptamer library as described herein. In other preferred embodiments, the monomeric aptamers are linked to each other by one or a plurality of linker polynucleotides to form multimeric aptamers. Monomeric aptamers can be linked to form multimeric aptamers by any suitable means and in any configurations. Exemplary multimeric aptamers are illustrated in FIG. 4A. In certain preferred embodiments, the monomeric aptamer comprises a first portion of a randomized sequence that is about 25 to 100 nucleotide (nt) in length, and in various other preferred embodiments, 30-100 nt, 30-60 nt, 25-70 nt, 25-60 nt, 40-60 nt, or 40-70 nt in length. In certain preferred embodiments, the randomized sequence is 45 nt in length.

In other preferred embodiments, the randomized sequence is flanked by at least one, preferably two, predetermined sequences of about 10-50 nt in length, and in various other embodiments, 15-40 nt, 15-30 nt, 20-40 nt, 25-30 nt, or 20-30 nt in length. In certain preferred embodiments, the predetermined sequence is 20 nt in length. In certain preferred embodiments, each monomeric aptamer comprises a randomized 45 nt sequence flanked by defined 20 nt sequences both upstream and downstream of the random sequence, i.e., the 5'-arm and 3'-arm, respectively. Computer programs are available to assist in designing the suitable predetermined sequence of the 5'-arm and 3'-arm regions to facilitate hybridization with the linker polynucleotide and to minimize potential secondary structure in the 5'-arm and 3'-arm regions. Exemplary computer program includes without limitation Mfold available at web site mobyle.pasteur.fr/cgi-bin/MobylePortal/portal.py?form=mfold.

In certain preferred embodiments of this aspect, randomized dimeric aptamers are formed wherein a linker polynucleotide comprises sequences complementary to both 5'-arm and/or 3'-arm region of random aptamers to form dimeric aptamers. In other preferred embodiments, trimeric or tetrameric aptamers are formed when a plurality of linker polynucleotides that hybridize to the 3'-arm and 5'-arm regions are introduced. In other preferred embodiments, the linker polynucleotide further comprises a single stranded hinge region situated in between the aptamer-binding motifs. In certain preferred embodiments, the hinge region is 3-10 nt in length; in various other preferred embodiments, the hinge region is 3-8 nt, 3-6 nt or 3-5 nt in length. In other preferred embodiments, the hinge region comprises sequence that is rich in As and Ts. The additional single stranded hinge region offers flexibility to allow the multimeric aptamers to coordinate and synergize multivalent interactions with target molecules or receptors.

As used herein, the term "randomized sequence" refers to an undefined nucleic acid molecule that contains degenerative nucleotide residues at some or all positions. Nucleic acid containing randomized sequence can be chemically synthesized by various methods known in the art and described herein.

As used herein, the term "predetermined sequence" refers to a defined nucleic acid molecule for which the nucleotide sequence is known. Nucleic acid containing randomized sequence can be chemically synthesized by methods known in the art and described herein or produced recombinantly in a cell.

In certain preferred embodiments, the predetermined sequence is complementary to at least 10 nt of sequence of the linker polynucleotide; in various other preferred embodiments, at least 15 nt, 20 nt, 25 nt, 30 nt, 35 nt, 40 nt, 45 nt or 50 nt of the sequence of the linker polynucleotide.

In certain preferred embodiments, the aptamers are further modified to protect the aptamers from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamer. For RNA aptamers, modified nucleotides such as substitutions of the 2'-OH groups of the ribose backbone, e.g., with 2'-deoxy-NTP or 2'-fluoro-NTP, can be incorporated into the RNA molecule using T7 RNA polymerase mutants (Epicentre Biotech, Madison, Wis.). The resistance of these modified aptamers to nuclease can be tested by incubating them with either purified nucleases or nuclease from mouse serum, and the integrity of aptamers can be analyzed by gel electrophoresis.

In certain preferred embodiments of this aspect of the invention, the aptamer, either monomeric or multimeric, can be covalently or non-covalently bound to one or more polynucleotides in the nucleic acid nanostructure; in other preferred embodiments, the aptamer binds to a connector polynucleotide that is directly or indirectly bound to the one or more polynucleotides in the nucleic acid nanostructure. Non-covalent binding includes without limitation nucleic acid base pairing of the aptamer directly with the polynucleotide of the nucleic acid nanostructure (one that remains partially unbound after formation of the nucleic acid nanostructure) or by way of a connector polynucleotide, or via biotin-streptavidin interaction.

The integrity of cell binding activities of the aptamers after binding to the nucleic acid nanostructure and/or after being modified to achieve nuclease resistance as described above can be tested by any suitable methods in the art, including without limitation flow cytometry and confocal fluorescent microscopy imaging to ensure that the binding to the nucleic acid nanostructure and/or modification does not compromise the cell binding activity.

Figure 3:
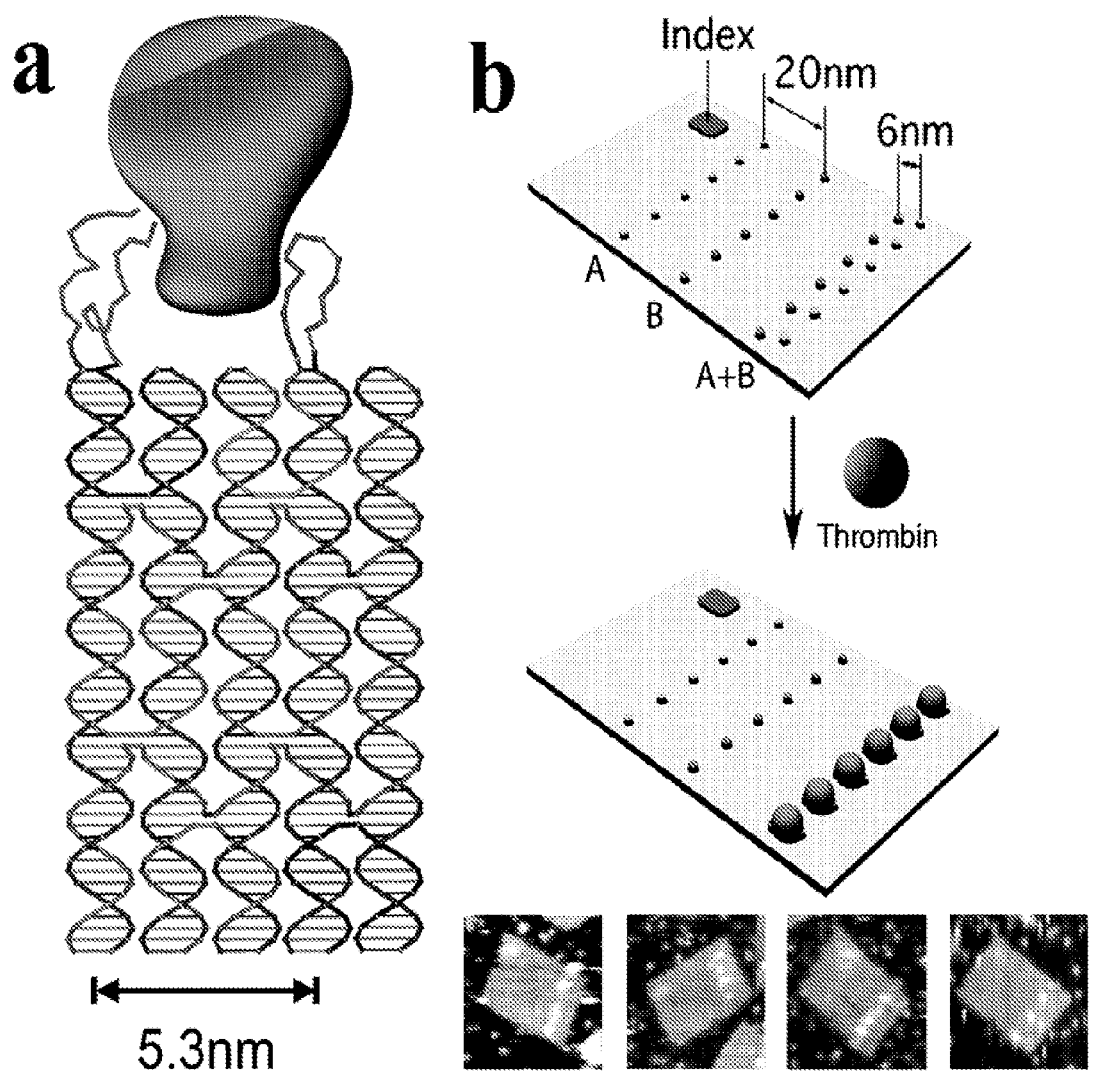
FIG. 3 shows multivalent binding of two aptamers against thrombin. a) Two thrombin aptamers are positioned on a five-helix DNA scaffold at optimized distance to improve the binding efficiency. b) Single molecule visualization of the bivalent aptamer-protein binding using AFM. In this case, aptamers are displayed in lines on a rectangular shaped DNA tile. The dual aptamer line possesses stronger binding affinity with protein than each individual aptamer lines.

In other preferred embodiments of this aspect, the first aptamer comprises a plurality of first aptamers, and/or the second aptamer comprises a plurality of second aptamers. Each of the first aptamer of the plurality of first aptamers and/or each of the second aptamer of the plurality of second aptamers can be a monomer or a multimer, such as a homomultimer or hetero-multimer. It was shown that aptamers positioned in close vicinity facilitate binding to the target molecule (see FIG. 3B). Suitable distance between each aptamer of the plurality of first aptamers and between each aptamer of the plurality of second aptamers on the nucleic acid nanostructure is determined by the distance that allows cross-linking of molecules, and coincides with the distance that promotes cooperative binding. In certain particular preferred embodiments, the distance of each second aptamer in the plurality of second aptamers is determined at a distance that facilitates trimerization of the death receptors upon aptamer binding. The suitable distance can be determined by any suitable methods in the art, including without limitation the method described herein. In certain embodiment, the distance between each aptamer of the plurality of first aptamers or between each aptamer of the plurality of second aptamers is from about 5 nm to about 15 nm; in various other preferred embodiments, between 5 nm and 8 nm; 6 nm and 8 nm; 10 nm and 13 nm; 10 nm and 15 nm; or 8 nm and 15 nm. Further, in certain other preferred embodiments, the distance between each first aptamer and second aptamer is from about 5 nm to about 15 nm; in various other preferred embodiments, between 5 nm and 8 nm; 6 nm and 8 nm; 10 nm and 13 nm; 10 nm and 15 nm; or 8 nm and 15 nm.

The distance between each aptamer of the plurality of aptamers on the nucleic acid nanostructure can be adjusted by changing the length of the aptamer nucleic acid or a connector polynucleotide by which the aptamer is bound to the nucleic acid nanostructure. In certain preferred embodiments, the adjustment of spacing is based on known parameters of B-DNA. For example, it is known that B-DNA is 3.4 angstrom per base pair rise, and 2 nm in diameter. In other preferred embodiments, the spacing can be adjusted by lengthening or shortening the aptamer sequences or the connector sequences. The spacing can be determined and verified by any suitable methods in the art, including without limitation atomic force microscopy (AFM) and Fluorescent Resonant Energy Transfer (FRET).

In certain preferred embodiments, the binding affinity for each aptamer-nucleic acid nanostructure with a defined spatial arrangement of aptamers is determined. In one embodiment, fluorophore-labeled aptamer-nucleic acid nanostructures are incubated with target cells and their binding activity is examined by flow cytometry. The binding affinity will be determined by the mean fluorescence intensity of target cells bound with fluorophore-labeled aptamers, as described by Tang et al., 2007, *Anal. Chem.* 79:4900. In certain preferred embodiments, the spacing between each aptamers of the same type or different types on the nucleic acid nanostructure can be adjusted to modulate binding affinity of the aptamers to the cell surface molecules or receptors.

In certain preferred embodiments, the distance between the first aptamer and the second aptamer on the aptamer-nucleic acid nanostructure is between about 5-15 nm; in various further preferred embodiments, between about 5-8 nm; 5-10 nm; 10-12 nm; 13-15 nm; 10-15 nm; or 8-15 nm.

In certain further preferred embodiments, the first aptamer comprises heteromultimeric aptamers that recognize at least two different binding sites on the same tumor cell; in certain other preferred embodiments, the second aptamer comprises heteromultimeric aptamers that recognize at least two different binding sites on the same death receptor.

In certain other preferred embodiments of this aspect, the first aptamer comprises a plurality of first aptamers that is specific for binding to at least two different tumor antigens on the surface of tumor cells; in certain other preferred embodiments, the second aptamer comprises a plurality of second aptamers that is specific for binding to at least two different death receptors. The multi-specific nature of the first aptamers allows better targeting and binding to one or multiple types of tumor cells, and the multi-specific nature of the second aptamers can achieve more efficient tumor cell killing and help circumvent the emergence of resistant tumor cells.

In certain preferred embodiments of this aspect, both the first aptamer and the second aptamer are each present on the nucleic acid nanostructure at a density of 2-20 aptamers per nucleic acid nanostructure; in various other preferred embodiments, between 2-15; 2-10; 4-20; 5-10; 4-15; 4-10; 2-9; 4-9; 4-8; 2-8; 4-6; or 2-6 aptamers per nucleic acid nanostructure. In certain preferred embodiments, the first aptamer is present on the nucleic acid nanostructure at a density of 5-10 aptamers per nucleic acid nanostructure, and the second aptamer is present at a density of 5-10 aptamers per nucleic acid nanostructure.

The density refers to the number of aptamers present on each nanostructure, where each aptamer is positioned in relation to other aptamer at a predetermined distance. For example, in certain preferred embodiments, the nucleic acid nanostructure contains 5-10 first aptamers, and each first aptamer is 5-8 nm away from any other first aptamers and 10-15 nm from any other second aptamers.

In certain particular preferred embodiments of this aspect, the ratio of first aptamers to second aptamers on the nucleic acid nanostructure is 1:1. In alternative preferred embodiments, the ratio of first aptamers to second aptamers on the nucleic acid nanostructure is 1:2, 1:3 or 1:4 to further enhance death-induction. In certain other preferred embodiments, the ratio of first aptamers to second aptamers on the nucleic acid nanostructure is 2:1, 3:1 or 4:1 to further enhance target tumor cell recognition.

In various further preferred embodiments, the composition comprises further aptamers (third, fourth, fifth, etc.) as may be suitable for a given intended use. All embodiments of the first and second aptamers apply to further aptamers.

Synthesis of polynucleotides is well known in the art. See, for example, Yan, H. et al., *Science* 2003, 301, 1882-1884; U.S. Pat. No. 6,255,469; WO 97/41142; Seeman, N. C., *Chem Biol,* 2003. 10: p. 1151-9; Seeman, N. C. *Nature,* 2003. 421: p. 427-431; Winfree, E. et al., *Nature,* 1998. 394: p. 539-44; Fu, T. J. and N. C. Seeman, *Biochemistry,* 1993. 32: p. 3211-20; Seeman, N. C., *J Theor Biol,* 1982. 99: p. 237-47; Storhoff, J. J. and C. A. Mirkin, *Chem. Rev.,* 1999. 99: p. 1849-1862; Yan et al., *PNAS* 100, Jul. 8, 2003 pp 8103-8108); and WO2006/124089. It is highly desirable, but not essential, in making the polynucleotides for the nucleic acid nanostructures to appropriately design sequences to minimize undesired base pairing and undesired secondary structure formation. Computer programs for such purposes are well known in the art. (See, for example, Seeman, N. C., *J Biomol Struct Dyn,* 1990. 8: p. 573-81). It is further preferred that the polynucleotides are purified prior to nucleic acid tile assembly. Purification can be by any appropriate means, such as by gel electrophoretic techniques.

As used herein, the term "nucleic acid nanostructure" or "nanostructure" refers to a nucleic acid structure that includes at least one nanoscale dimension, wherein the nucleic acid structure comprises one or more single stranded nucleic acids, which hybridize to form at least a partially double-stranded structure with defined features and geometry. The nucleic acid nanostructure presents ligands bound thereto to the target cell surface molecules, including a death receptor, on a tumor cell, and the resulting binding promotes death-receptor mediated tumor cell death. In some preferred embodiments, the nucleic acid nanostructure comprises a double-stranded DNA linker molecule. In preferred embodiments, the nucleic acid nanostructure comprises a DNA nanostructure. In certain preferred embodiments, the nucleic acid nanostructure comprises a DNA tile; in certain other preferred embodiments, the nucleic acid nanostructure comprises a DNA tiling array.

A variety of suitable nucleic acid nanostructures are known in the art. See for example, WO2008/033848 and WO2006/124089, and Ke et al., 2008, *Science* 319: 180-183, the disclosures of which are incorporated herein by reference in their entireties. In certain preferred embodiments, the nucleic acid nanostructure comprises a spiral DNA scaffold, a DNA origami, or a DNA tile or tiling array. Such nucleic acid nanostructures are formed by base pairing of single stranded DNA or derivatives thereof or by other non-covalent linkage, such as biotin-streptavidin interaction.

In certain preferred embodiments of this aspect, the nucleic acid nanostructure comprises a multi-helical bundle to display ligands. In certain preferred embodiments, the ligands are aptamers. The multi-helical bundle comprises 2-20 double stranded helices; in various other preferred embodiments, the multi-helical bundle comprises 2-15, 2-12, 2-10, 3-20, 3-12, 3-10, 4-20, 4-10, 4-8 double stranded helices. It is within the skill of one of ordinary skill in the art to determine the suitable number of double stranded helices suitable for use as nucleic acid nanostructure in the present invention. In certain preferred embodiments, the nucleic acid nanostructure is 50-2000 nm (i.e., 50×50 nm$^2$ to 2000×2000 nm$^2$); in other preferred embodiments, 10-200 nm; 25-200 nm; 25-100 nm; 50-200 nm; 50-150 nm; 50-100 nm; 100-200 nm; 100-300 nm; 300-500 nm; 300-800 nm; 800-1000 nm; 1000-1500 nm; 1300-1800; or 1500-2000 nm in length. In certain preferred embodiments, the nucleic acid nanostructure is 100 nm in length (i.e.: 100×100 nm$^2$) or 100-2000 nm in length.

In certain preferred embodiments of the invention, the nucleic acid nanostructure comprises one or more nucleic acid tiles, preferably DNA tiles. In certain other preferred embodiments, the nucleic acid nanostructure comprises a DNA tiling array. Self-assembling nucleic acid tiling lattices represent a versatile system for nanoscale construction. Structure formation using nucleic acid 'smart tiles' begins with the chemical synthesis of single-stranded polynucleotides, which when properly annealed, self-assemble into nucleic acid tile building blocks through Watson-Crick base pairing. DNA tiles bearing complementary sticky ends are then able to further self-assemble into larger arrays with distinct topological and geometric features. A self-assembling, finite nucleic acid-based nanoarray allows a wide variety of discrete molecules to be placed at specific locations with nm-scale accuracy. Various nucleic acid tiles and tiling array have been described in the art. See for example WO2008/033848 and WO2006/124089, the disclosures of which are incorporated herein by reference in their entireties.

The dimensions of a given nucleic acid tile can be programmed, based on the length of the polynucleotides of the nucleic acid nanostructure (i.e., those polynucleotides that are integrally involved in the structure of the nucleic acid tile) and their programmed shape and size, the length of the sticky ends (when used), and other design elements. Based on the teachings provided herein and known in the art, those of skill in the art can prepare nucleic acid tiles of any desired size. In various preferred embodiments the length and width of individual nucleic acid tiles are between 3 nm and 100 nm; in various other preferred embodiments, widths range from 4 nm to 60 nm and lengths range from 10 nm to 90 nm. In certain preferred embodiments, the nucleic acid nanostructure comprises a singe nucleic acid tile or a nucleic acid tiling array that has a dimension consistent with the dimension of a nucleic acid nanostructure as described above suitable for use in the present invention.

The dimensions of nucleic acid tiling arrays can also be programmed with the use of boundary tiles (i.e., tiles designed to terminate further assembly of the array), depending on the size of the individual nucleic acid tiles, the number of nucleic acid tiles, the length of the sticky ends (when used), the desired spacing between individual nucleic acid tiles, and other design elements. In embodiments that do not incorporate boundary tiles, the size of the arrays depends on the purity of the DNA strands, the stoichiometry of the different polynucleotides, and the kinetics (how slow the annealing process is). Based on the teachings herein and known in the art, those of skill in the art can prepare nucleic acid tiling arrays of any desired size. In certain preferred embodiments, the nucleic acid tiling array is within a size limit that does not induce internalization of the tiling array by way of phagocytosis of the cell. In certain preferred embodiments, the nucleic acid tile or tiling array is not more than 100 nm in length (i.e.: 100×100 nm$^2$).

In certain particular preferred embodiments, the aptamer-nucleic acid nanostructure is of a size sufficient to trigger passive phagocytosis of the ligand-nucleic acid nanostructure by the cells. In certain preferred embodiments, the composition comprises an aptamer-nucleic acid nanostructure that is between about 100 nm and about 2 µm in length (i.e., 100× 100 nm$^2$ to 2000×2000 nm$^2$); in various other preferred embodiments, 100-200 nm, 100-300 nm, 300-500 nm, 300-800 nm, 800-1000 nm, 1000-1500 nm, 1300-1800, or 1500-2000 nm in length.

In certain embodiments, the aptamer-nucleic acid nanostructure further comprises a transduction domain. As used herein, the term "transduction domain" means one or more amino acid sequence or any other molecule that can carry the intracellular nucleic acid nanostructure across cellular membranes. (See, for example, *Cell* 55: 1179-1188, 1988; *Cell* 55: 1189-1193, 1988; *Proc Natl Acad Sci USA* 91: 664-668, 1994; *Science* 285: 1569-1572, 1999; *J Biol Chem* 276: 3254-3261, 2001; and *Cancer Res* 61: 474-477, 2001). Any transduction domains that can lead a molecule across cellular membranes are suitable for use in the present invention. In further embodiments, the nucleic acid nanostructure comprises at least one transduction domain selected from the group consisting of (R)$_{4-9}$ (SEQ ID NO:43); GRKKRRQR-RRPPQ (SEQ ID NO:44); AYARAAARQARA (SEQ ID NO:45); DAATATRGRSAASRPTERPRAP ARSASR-PRRPVE (SEQ ID NO:46); GWTLNSAGYLLGLINLKA-LAALAKKIL (SEQ ID NO:47); PLSSIFSRIGDP (SEQ ID NO:48); AAVALLPAVLLALLAP (SEQ ID NO:49); AAV-LLPVLLAAP (SEQ ID NO:50); VTVLALGALAGVGVG (SEQ ID NO:51); GALFLGWLGAAGSTMGAWSQP (SEQ ID NO:52); GWTLNSAGYLLGLINLKALAALAKKIL (SEQ ID NO:53); KLALKLALKALKAALKLA (SEQ ID NO:54); KETWWETWWTEWSQPKKKRKV (SEQ ID NO:55); KAFAKLAARLYRKAGC (SEQ ID NO:56); KAF-AKLAARLYRAAGC (SEQ ID NO:57); AAFAKLAAR-LYRKAGC (SEQ ID NO:58); KAFAALAARLYRKAGC (SEQ ID NO:59); KAFAKLAAQLYRKAGC (SEQ ID NO:60), and AGGGGYGRKKRRQRRR (SEQ ID NO:61). In certain embodiments, the aptamer-nucleic acid nanostructure comprising a transduction domain further comprises one or more modifications to the nucleic acid that facilitate phagocytosis as described above.

In one preferred embodiment, the nucleic acid nanostructure comprises or consists of a nucleic acid tiling array, comprising a plurality of nucleic acid tiles joined to one another via sticky ends, wherein each nucleic acid tile comprises one or more sticky ends, and wherein a sticky end for a given nucleic acid tile is complementary to a single sticky end of another nucleic acid tile in the nucleic acid tiling array; wherein the nucleic acid tiles are present at predetermined positions within the nucleic acid tiling array as a result of programmed base pairing between the sticky ends of the nucleic acid tiles. In this embodiment, one or more tiles in the array comprise nucleic acid probes for binding the ligands to the nanostructure.

As used herein, "programmed base pairing" means that the sticky ends for the different nucleic acid tiles are designed to ensure interactions of specific nucleic acid tiles through their complementary sticky ends, thus programming the position of the nucleic acid tile within the nucleic acid tiling array. As used herein, "predetermined positions" means that the ultimate position of each nucleic acid tile in the self-assembled nucleic acid tiling array is based on the sequence and position of its sticky ends and the sequence and position of the sticky ends of the other nucleic acid tiles in the nucleic acid tiling array, such that the plurality of nucleic acid tiles can only assemble in one specific way.

Since the position of all nucleic acid tiles in the array is predetermined, the boundary tiles are also predetermined, and thus the nucleic acid tiling arrays of the present invention have defined boundaries (i.e.: "finite" nucleic acid tiling arrays).

Each "nucleic acid tile" comprises (a) a structural element (also referred to herein as the polynucleotide "core") constructed from a plurality of nucleic acid polynucleotides; and (b) 1 or more "sticky ends" per nucleic acid tile attached to the polynucleotide core. Those of skill in the art are well aware of the wide range of such polynucleotide cores, including but not limited to 4 arm branch junctions, 3 arm branch junctions, double crossovers, triple crossovers, parallelograms, 8 helix bundles, 6-tube formations, and structures assembled using one or more long strands of nucleic acid that are folded with the help of smaller 'helper' strands (See, for example, Yan, H. et al., *Science* 2003, 301, 1882-1884; U.S. Pat. No. 6,255,469; WO 97/41142; Seeman, N. C., *Chem Biol,* 2003. 10: p. 1151-9; Seeman, N. C. *Nature,* 2003. 421: p. 427-431; Winfree, E. et al., *Nature,* 1998. 394: p. 539-44; Fu, T. J. and N. C. Seeman, *Biochemistry,* 1993. 32: p. 3211-20; Seeman, N. C., *J Theor Biol,* 1982. 99: p. 237-47; Storhoff, J. J. and C. A. Mirkin, *Chem. Rev.,* 1999. 99: p. 1849-1862; Yan et al., *Proceedings of the National Academy of Sciences* 100, Jul. 8, 2003 pp 8103-8108.)

Self-assembly of a plurality of nucleic acid tiles results in programmed base-pairing interactions between sticky ends on different nucleic acid tiles to form the nucleic acid tiling arrays.

As used herein, a "plurality" of nucleic acid tiles means 4 or more nucleic acid tiles. In various preferred embodiments, the nucleic acid tiling array contains at least 6, 9, 16, 25, 36, 49, 64, 81, 100, 121, 144, 169, 206, 225, 256, 289, 324, 361, or 400 nucleic acid tiles.

As used herein, the term "nucleic acid probe" refers to a nucleic acid sequence synthesized as part of one or more core polynucleotide structure in the nucleic acid tile that does not participate in base pairing with other core polynucleotide structures or adjacent nucleic acid tiles. Thus, the nucleic acid probe is available for interactions with various "targets" to which it binds directly or indirectly.

As used herein, a "nucleic acid tiling array" is the assembled array of nucleic acid tiles of the invention based on specific Watson-Crick base pairing between sticky ends of different nucleic acid tiles. Each nucleic acid tile within the nucleic acid tiling array is located at a pre-determined position in the array, based on the complementarity of its "sticky ends" to sticky ends on a different nucleic acid tile. As will be apparent to those of skill in the art, a given nucleic acid tile may specifically bind to only one other nucleic acid tile in the nucleic acid tiling array (if the given nucleic acid tile is programmed with only a single sticky end), or it may interact with 2, 3, 4, 5, 6, 7, 8, 9, 10, 11, 12, or more other nucleic acid tiles in the nucleic acid tiling array if the given nucleic acid tile has 2, 3, 4, 5, 6, 7, 8, 9, 10, 11, 12, or more sticky ends, respectively. For example, closely packed arrays typically utilize 2-12 sticky ends, but more sticky ends might be used in an array that branched from a central point, as in a dendrimeric nucleic acid tiling array.

As discussed above, the nucleic acid tiles in the tiling array include "boundary tiles", nucleic acid tiles that are programmed for self-assembly at the edge of the nucleic acid tiling array based on their sticky end composition. As a result, the nucleic acid tiling array is finite. In a preferred embodiment, one or more boundary tiles in the nucleic acid tiling array further comprise modification of one or more polynucleotides that terminate further self-assembly. In a non-limiting example, the modification comprises addition of "TTT" (or some other sequence that has no complement within the array) overhangs at the parts of each tile that lies at the edge of the array (or adjacent to holes in it) such that the array must not be continued beyond those points. Alternatively, no sticky ends are placed on those sections of the tiles that lie at the edges of the arrays, terminating them instead with blunt-ended nucleic acid, such as double helical DNA (and thus these boundary tiles only have sticky ends to tie into the existing array, but not to extend it).

In a further embodiment, sticky-ends can be added to the edge of the finite size arrays, thus allowing hierarchical assembly of larger arrays with defined dimensions. In this embodiment, sticky ends that are not complementary to any of the stick ends on the nucleic acid tiling array, are added to the edge of the array to permit complementary binding to any other structure of interest, such as a second finite array.

In a further preferred embodiment, the nucleic acid tiling array comprises an indexing feature to orient the tiling array and thus facilitate identification of each individual nucleic acid tile in the array. Any indexing feature can be used, so long as it is located at some spot on the array that has a lower symmetry than the array itself Examples of such indexing features include, but are not limited to: (1) including one or more tiles that impart(s) an asymmetry to the array; (2) including one or more tiles that is/are differentially distinguishable from the other tiles (for example, by a detectable label); for example, a biotin molecule that could later be marked by exposing the array to streptavidin; (3) including any protrusion on an edge of the array that is offset from two edges by unequal amounts, which will serve to index the array even if it is imaged upside down; (4) including a high point on the array that is detectable; (5) introducing one or more gaps in the tiling array that introduce a detectable asymmetry; and (6) making the nucleic acid tiling array of low enough symmetry with respect to rotations and inversions that locations on it could be identified unambiguously; for example, a nucleic acid tiling array in the shape of a letter "L" with unequal sized arms would serve such a purpose.

As used herein, a "sticky end" is a single stranded base sequence attached to the polynucleotide core of a nucleic acid tile. For each sticky end, there is a complementary sticky end on a different nucleic acid tile with which it is designed to bind, via base pairing, within the nucleic acid tiling array. Each nucleic acid tile must contain at least one sticky end (for example, in a boundary nucleic acid tile of certain embodiments), but may contain 2, 3, 4, 5, 6, 7, 8, 9, 10, 11, 12, or more sticky ends, depending on the design of the nucleic acid tiling array.

The sticky ends are incorporated into the nucleic acid tile as a portion of one or more of the core polynucleotides. Such incorporation can be carried out in a variety of ways, in part depending on the type of polynucleotide core used.

The length of the sticky ends for each nucleic acid tile can vary, depending on the desired spacing between nucleic acid tiles, the number of nucleic acid tiles in the nucleic acid tiling array, the desired dimensions of the nucleic acid tiling array, and any other design parameters such as the desired distance between ligands attached to the array. The sticky ends do not have to be of identical length for a given nucleic acid tile or relative to other nucleic acid tiles in the nucleic acid tiling array, so long as a complementary sticky end of an identical length is present on the nucleic acid tile to which it is designed to base pair. Alternatively, the sticky ends on all of the nucleic acid tiles can be of identical length. Particularly preferred lengths of the sticky ends are 4, 5, 6, 7, 8, 9, or 10 nucleotides.

In one preferred embodiment, each sticky end for a given nucleic acid tile is (a) different than the other sticky ends for that nucleic acid tile; (b) unique to that nucleic acid tile with respect to all other nucleic acid tiles in the array; and (c) complementary to a single sticky end of one other nucleic acid tile in the nucleic acid tiling array. As will be apparent to those of skill in the art, the polynucleotide structural element of each nucleic acid tile can be identical in this embodiment, so long as the sticky ends are unique. Thus, in this embodiment, a nucleic acid tiling array with "N" tiles is made by synthesizing "N" different tiles, each containing unique sticky-ends to connect to its neighboring tiles, so that each tile takes up a unique and well defined position in the array.

In a preferred embodiment, the nucleic acid tiles are not all unique (i.e.: some of the nucleic acid tiles may contain the same sticky ends). The nucleic acid tiling strategy in this embodiment takes advantage of the geometric symmetry of the nucleic acid tiling array. In general, to use a total of N tiles to construct a fixed size 2D nucleic acid tiling array with $C_m$ symmetry, where m=2, 3, 4, or 6, the number of unique tiles the fixed size array requires is N/m, if N/m is an integral number, or Int (N/m)+1, if N/m is an non-integral number. This strategy is cost-effective in material, particularly when combined with embodiments where the polynucleotide structural element for each nucleic acid tile is identical. This embodiment minimizes polynucleotide design time and the sample preparation time dramatically. In these embodiments, the total number of unique sticky end pairs is preferably N*(N−1)/2.

In a preferred embodiment of each of the above embodiments, each nucleic acid tile comprises an identical polynucleotide structural element, which limits the number of different polynucleotides that must be synthesized and assembled. In this embodiment, the nucleic acid tiles differ in their sticky ends, which program the predetermined position of each nucleic acid tile in the nucleic acid tiling array. As disclosed below, the nucleic acid tiles in this and all other embodiments may contain further components in addition to the polynucleotide structural element and the sticky ends, and these further components may differ between different nucleic acid tiles.

In a preferred embodiment, the resulting nucleic acid tiling array is "non-periodic," meaning that the array does not include simple repetitive nucleic acid tile "patterns," such as ABABAB; ABCDABCD; ABABDCDCABABDCDC. This does not require that all of the tiles in the array be unique.

In another preferred embodiment, the nucleic acid nanostructure comprises or consists of a nucleic acid thread strand-based tile, comprises: (a) a nucleic acid thread strand; (b) a plurality of helper nucleic acid strands that are complementary to parts of the nucleic acid thread strand; wherein a plurality of the helper nucleic acid strands further comprises a nucleic acid probe; and wherein the nucleic acid thread strand is folded into a desired shape by hybridization to the helper strands; wherein the nucleic acid thread strand is not complementary to any of the nucleic acid probes, and wherein the predetermined size of the array is determined by the length and shape of the nucleic acid thread strand as folded by helper strands.

As used herein, "the nucleic acid thread strand is not complementary to any of the nucleic acid probes" means that the nucleic acid probes do not base pair with the thread strand over the length of the nucleic acid probe under the conditions used, and thus the helper strands are available for interactions with a target. In this embodiment, no sticky ends are required for self-assembly.

The nucleic acid thread strand can be any suitable polynucleotide of appropriate length and sequence for the desired nucleic acid tile. In one embodiment, the nucleic acid thread strand is a genomic nucleic acid strand, or suitable fragments thereof, such as from a virus, bacterium, or indeed any organism from which long DNA can be extracted. The only caveat is that the chosen section of genomic nucleic acid should not have sequences that are complementary to the probe sequences, and they should not contain significant amounts of repeated sequences or other sequences that might form structures that interfere with assembly of the array (such the G-rich regions that might form quadruplexes as in telomere DNA).

In a preferred embodiment, genomic nucleic acid, or fragments thereof, is used as the nucleic acid thread for lengths above about 50 bp where synthetic nucleic acid becomes expensive and difficult to make. Lengths up to the full length of an organism's genome (ca. $10^9$ bp) are feasible if they met the sequence criteria described above.

The nucleic acid helper strands are complementary to regions of the nucleic acid thread and not to each other, and are designed to hybridize to the nucleic acid thread strand so as to constrain the nucleic acid thread strand into a desired shape. A plurality of the nucleic acid helper strands comprises nucleic acid probes. In one embodiment, helper strands are between 10 and 50 nucleotides, not including any DNA probe that is part of the helper strand.

In a further embodiment, the nucleic acid thread-based tile further comprises nucleic acid filler strands that hybridize to the nucleic acid thread strand. These strands are not involved in shaping the nucleic acid thread strand, but add further structural integrity to the resulting nucleic acid tile. It is further preferred that a plurality of the nucleic acid filler strands further comprises a nucleic acid probe.

In another embodiment, one or more of the helper strands can be part of a larger nucleic acid structure. In one example, one or more helper strands protrude from one or more nucleic acid tiles. The helper strands fold the thread strand into place, and the nucleic acid tiles (and their nucleic acid probes) comprising the helper strands are thus precisely positioned on the thread strand.

In another embodiment, one or more of the helper strands may protrude from one or more nucleic acid arrays (formed by combining two or more nucleic acid tiles). In this embodiment, one or more helper strands protrude from one or more tiling arrays and fold the thread strand into place, and the tiling arrays (and the nucleic acid tiles they are composed of, including nucleic acid probes) comprising the helper strands are thus precisely positioned on the thread strand. In this embodiment, it is possible, for example, to provide unlimited hierarchies of nucleic acid tiling arrays.

The dimensions of a given nucleic acid thread strand-based tile can be programmed, based on the available length and sequence of thread strand nucleic acid, and other design elements. For example, a 10,000 base thread strand nucleic acid could be formed into a nucleic acid tile covering an area of approximately 2 nm×10,000×0.3 nm or $6×10^{-15}$ m$^2$. This would correspond to a square of about 0.1 µm on each side. Depending upon the design of the thread strand-based nucleic acid tile, the size of the nucleic acid probe, the specific target, and other design feature, the density of target molecules on the nucleic acid tile can be as high as $10^{12}$ per square cm.

In this most preferred embodiment, the nucleic acid thread-based tile can be assembled in one step. A long template strand of nucleic acid is mixed with shorter 'helper' strands, usually in a large molar excess of the shorter strands. The strand sequences are chosen to fold the long template strand into the desired shape, as described by Yan et al. (Proceedings of the National Academy of Sciences 100, Jul. 8, 2003 pp 8103-8108.) The probe array is then achieved by using one or more helper strands with nucleic acid probes that are not complementary to any part of the template strand or the other helper strands. These will then protrude from the array, forming single stranded probe strands at known locations if the array contains an index feature. General conditions for such hybridization are known in the art.

Figure 6:
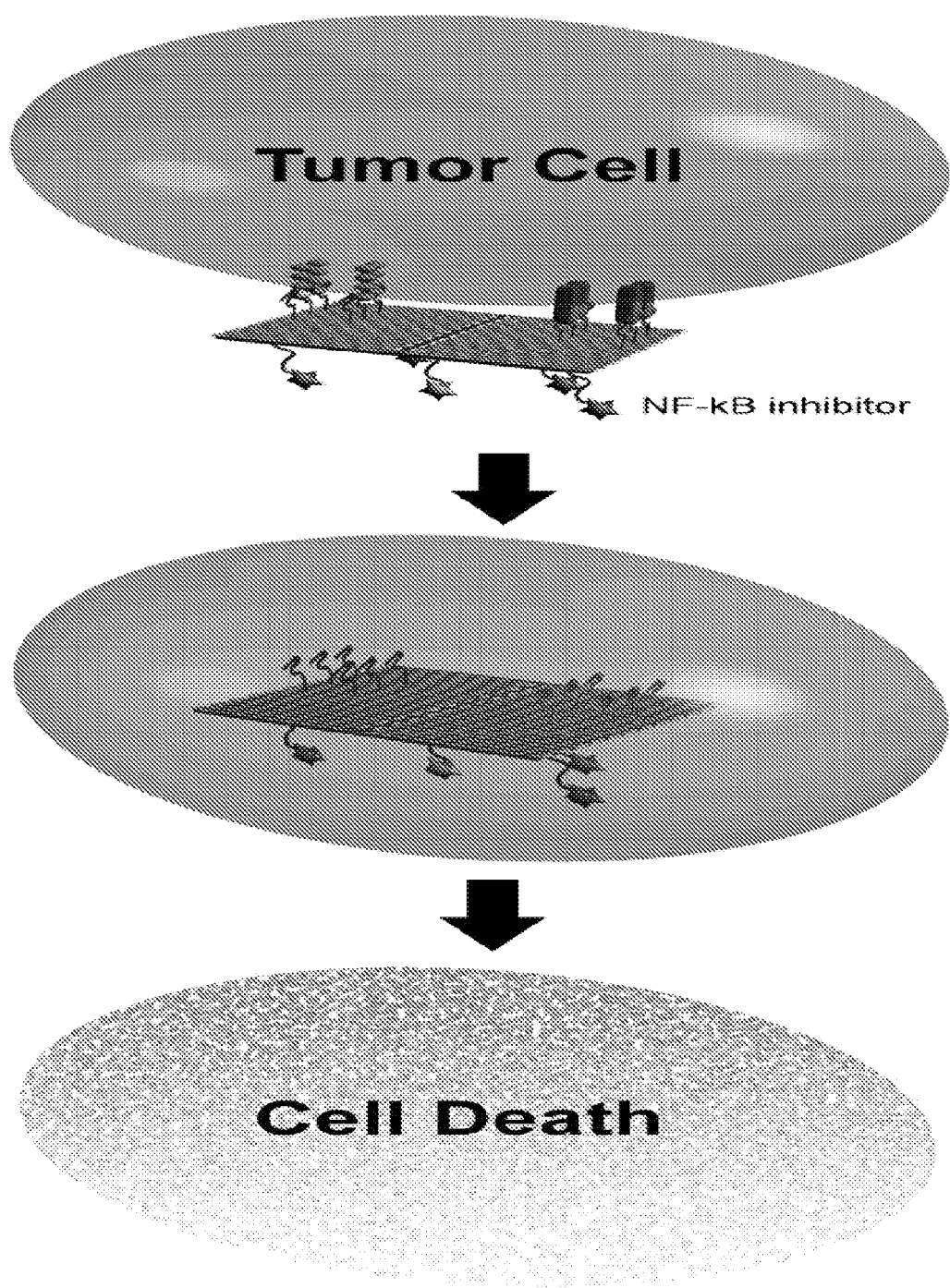
FIG. 6 presents a diagram illustrating synergized apoptosis of tumor cells by a multifunctional aptamer-nucleic acid nanostructure containing tumor-specific aptamers, agonistic aptamers to TRAIL-Rs and apoptosis-inducers, such as NF-κB inhibitors (illustrated in stars).

The scalable feature of the aptamer-nucleic acid nanostructure makes it easy to assemble additional immune modulating ligands to synergize the cell-death pathways and maximize cancer cell killing. In certain advantageous embodiments, the aptamer nucleic acid nanostructure of the invention further comprises an apoptosis inducer that is bound to the nucleic acid nanostructure. Suitable apoptosis inducers for use in the instant invention include without limitation shRNA, siRNA, decoy oligonucleotides for STAT3 or NF-κB. Exemplary decoy oligonucleotides include double stranded deoxyoligonucleotides with a hairpin end containing single or multiple copies of NF-κB binding site (GGATTTCCC) or STAT3 binding site (CATTTCCCGTAAATC, SEQ ID NO:33), such that these oligonucleotides can bind to NF-κB or STAT3, blocking the NF-κB- or STAT3-mediated anti-apoptotic responses in the cells. NF-κB activation is known to protect cells from apoptosis and NF-κB inhibitors can sensitize tumor cells to targeted apoptosis by TRAIL-R agonists (Franco et al., 2001. *J Immunol* 166:5337-5345). Thus, in certain preferred embodiments, the apoptosis inducer is an NF-κB inhibitor; in certain other preferred embodiments, the NF-κB inhibitor is a NF-κB decoy oligonucleotide as illustrated in FIG. 6. Without being limited to certain specific mechanisms, in certain preferred embodiments, once the aptamer-nucleic acid nanostructure is internalized inside the tumor cell, the apoptosis inducer can trigger and activate the intrinsic apoptosis pathway to facilitate tumor cell killing. The assembled aptamer nucleic acid nanostructure is analogous to a "Trojan Horse" in the sense that it carries an array of arsenals of predetermined amounts to the target tumor cells to induce apoptosis.

In certain other preferred embodiments, alternative or additional apoptosis-sensitizing molecules can be included in the aptamer-nucleic acid nanostructure. For example, interfering RNA (RNAi), which can down-regulate the expression of several anti-apoptotic genes, such as survivin, bcl-2 and cFLIP, can be readily inserted into the aptamer-nucleic acid nanostructure. In certain preferred embodiments, the RNAi becomes dissociated from the nanostructure and enters the nucleus after the aptamer-nucleic acid nanostructure is internalized into the tumor cell.

In certain preferred embodiments the nucleic acid nanostructure comprises one type of apoptosis inducers present at a density of 2-10, 2-5, 4-10, 4-8, 5-10, 8-10 per nucleic acid nanostructure. In other preferred embodiments, the apoptosis inducers are present at a density of 4-10 per nucleic acid nanostructure. In certain other preferred embodiments, the nucleic acid nanostructure comprises at least two types of apoptosis inducers each present at a density of 2-10, 2-5, 4-10, 4-8, 5-10, 8-10 per nucleic acid nanostructure. In certain preferred embodiments, each type of apoptosis inducers is present at a density of 4-10 per nucleic acid nanostructure. In certain other preferred embodiments, the two types of apoptosis inducers are present at a ratio of 1:1, 1:2, or 1:3. In certain preferred embodiments, the nucleic acid nanostructure comprises NF-kB and STAT3 decoy oligonucleotides. In certain preferred embodiments, these two types of apoptosis inducers are present at a ratio of 1:1.

Such multi-functional aptamer-nucleic acid nanostructures described herein comprising tumor-targeting and tumor-killing activities are advantageous for target-specific cancer treatment. Attempts have been made to develop nano-carriers as delivery platforms to assemble multi-functional molecules, such as drugs, genes and vaccines, in liposomes or virus-like particles (VLPs) for treating cancer or immunodisorders (Jabr-Milane et al., 2008, *J Control Release* 130:121-128; Peek et al., 2008, *Adv Drug Deliv Rev* 60:915-928). The inventive aptamer-nucleic acid nanostructure, however, provides the critical spatial arrangement or precise ratio control that is not possible in other systems. TRAIL-induced apoptosis are dependent on the cross-linking and/or oligomerization of their cognate receptors, which is greatly facilitated by the adjustable structural configurations of the aptamers on the nucleic acid nanostructure as described herein.

The inventive nucleic acid nanostructure can be designed by incorporating 5-10 nucleotides single-stranded oligo-dT to increase flexibility—incorporation of longer single-stranded oligo-dT increases flexibility and reduces rigidity of the nucleic acid nanostructure. See Hasegawa et al., 2008. *Sensors* 8:1090-1098. The rigidity and well-defined geometry of nucleic acid nanostructures provide superb spatial and orientational control of the ligands on the array. The spacing of the ligands and their positioning with respect to, for example, a tiling array surface can be precisely controlled to the sub-nanometer scale. This not only allows optimization of geometry for fast kinetics, it also allows efficient rebinding of the receptor to nearby ligands and leads to improved binding efficiency. The well separated positioning of the ligands/aptamers on the array also allows efficient binding of different receptors to bind corresponding ligands or aptamers on the tiling array.

As will be apparent to those of skill in the art, in this embodiment, not all of the nucleic acid tiles in a nucleic acid tiling array are required to possess an aptamer. Thus, one or more of the nucleic acid tiles in the nucleic acid tiling array comprises an aptamer; preferably a majority of the nucleic acid tiles in the array comprise an aptamer; more preferably all of the nucleic acid tiles comprise an aptamer.

All embodiments of aptamers, linkers, etc. described herein are applicable to this aspect of the invention as well. All embodiments of this aspect can be applied to any other aspects of the invention.

In yet another aspect, the invention provides methods of making an aptamer-nucleic acid nanostructure, the method comprising contacting a first aptamer, a second aptamer, and at least one polynucleotide under conditions suitable for binding of the first and second aptamers to the polynucleotide to form an aptamer-DNA nanostructure, wherein the first aptamer is specific for binding to a tumor cell and the second aptamer is specific for binding to a death receptor on the tumor cell, and wherein the polynucleotide forms a nucleic acid nanostructure. In certain preferred embodiments, the first and second aptamers directly bind to the polynucleotide, or indirectly through a connector polynucleotide or a nucleic acid probe that is bound to the polynucleotide. In various other preferred embodiments, the first and second aptamers bind to the polynucleotide non-covalently by ways of, including without limitation, base pairing and biotin-streptavidin interaction. In certain preferred embodiments of this aspect, the polynucleotide is part of a nucleic acid tile.

In another embodiment, the aptamer-nucleic acid nanostructure comprises a plurality of polynucleotides, and wherein the contacting is done under conditions suitable to promote hybridization of the plurality of polynucleotides into at least one nucleic acid tile. In yet further preferred embodiments, the plurality of polynucleotides forms a plurality of nucleic acid tiles, and wherein the plurality of nucleic acid tiles forms at least one nucleic acid tiling array.

The particular hybridization buffers and other conditions employed can vary depending on the polynucleotide lengths and sequences, and are well within the level of skill in the art based on the teachings herein. Any suitable hybridization conditions known in the art can be adopted. Exemplary hybridization conditions are provided as follows. The nucleic acid nanostructures carry a considerable negative charge at low salt, and therefore hybridization in the presence of a significant amount of salt (e.g., 10 mM $MgCl_2$ or 600 mM or greater monovalent salt like NaCl) is preferred. Other typical annealing conditions include 1 M NaCl, 10 mM $NaHPO_4$ (pH7). Aptamers (when included as ligands) typically require 10 mM $MgCl_2$ to fold properly. General parameters for hybridization conditions for nucleic acids are described in Sambrook et al., supra, and in Ausubel et al., 1987, Current Protocols in Molecular Biology, Greene Publishing and Wiley-Interscience, New York.

In certain preferred embodiments, the stoichiometric amount of each polynucleotide in a nucleic acid nanostructure is combined under denaturing conditions, such as between 90° C. and 99° C., followed by cooling to between 25° C. and 50° C. in appropriate hybridization buffer, as can be determined by those of skill in the art. In a preferred embodiment, annealing protocols involve a high temperature and low salt denaturing step, followed by a low temperature high salt annealing step. In this embodiment, the high salt concentrations are not added to the reaction until the polynucleotides are removed from the heat and placed on ice.

The polynucleotide concentration used can vary, and those of skill in the art, based on the teachings provided herein and known in the art, can determine appropriate concentrations. In one embodiment, polynucleotide concentration is between 1 nm and 10 µM.

In certain preferred embodiments, the nucleic acid nanostructure comprises a plurality of nucleic acid tiles that is combined under conditions suitable to promote hybridization of the sticky ends between different nucleic acid tiles. In a preferred embodiment, such suitable conditions include incubation in appropriate hybridization solution at a beginning temperature of between 25° C. and 45° C., followed by cooling in the same hybridization buffer to between 5° C. and 25° C. over 1 hour to 24 hours. The specific condition chosen need to balance the needs between avoiding disassembly of the tiles, which generally have melting temperatures in the range of 50-65° C., and to eliminate the possible mismatches among the different sticky ends of the tiles. In a preferred embodiment, the buffer condition used comprises 40 mM Tris, 20 mM acetic acid, 2 mM EDTA, and 12.5 mM magnesium acetate, pH 8.0.

In a preferred embodiment, synthesis of the nucleic acid tiling arrays comprises separating free nucleic acid tiles and/or incompletely hybridized nucleic acid tiles from completely formed nucleic acid tiling arrays. Any appropriate separation method can be used, including but not limited to size exclusion chromatography, sucrose gradient centrifugation, and affinity based separation techniques. In a preferred embodiment, the nucleic acid tiling arrays are chemically modified so as to permit affinity-based separation techniques. Any chemical modification that permits such affinity-based separation techniques can be used, including but not limited to, chemically modifying the nucleic acid tiling array to contain one or more biotin residues, which can then be used for streptavidin-based affinity separation of the nucleic acid tiles.

The aptamer-nucleic acid nanostructures of the invention can be made and stored as described herein. In various preferred embodiments, the aptamer-nucleic acid nanostructures may be present in solution, or in lyophilized form. All the preferred embodiments of this aspect of methods of making an aptamer-nucleic acid nanostructure can be used in conjunction with in any other aspects of the invention.

In yet another aspect, the invention provides a method of treating a tumor in a mammal comprising administering to a mammal in need thereof an amount effective to treat the tumor of a composition comprising a first ligand that is specific for a tumor cell, and a second ligand that is specific for a death receptor on the tumor cell, wherein the first and second ligands are bound to a nucleic acid nanostructure. In certain preferred embodiments, the first ligand is a first aptamer and the second ligand is a second aptamer.

Without being bound or limited to a particular mechanism, in certain preferred embodiments, the first aptamer binds to tumor antigen on a tumor cell and the second aptamer binds to a TRAIL receptor on the tumor cell, wherein the aptamer nucleic acid nanostructure targets specifically to tumor cells by the binding of the first aptamer with the tumor antigen, and triggers TRAIL receptor oligomerization and apoptosis of the tumor cell by the binding of the second aptamer to the TRAIL receptor.

As used herein, the terms "treatment" and "treating" means (i) preventing the disease; for example, preventing a disease, condition or disorder in an individual who may be predisposed to the disease, condition or disorder but does not yet experience or display the pathology or symptomatology of the disease, such as preventing tumor growth and/or metastasis; (ii) limiting the disease; for example, limiting a disease, condition or disorder in an individual who is experiencing or displaying the pathology or symptomatology of the disease, condition or disorder; for example, limiting tumor growth and/or metastasis, or limiting the rate of tumor growth and/or metastasis, or extending patient survival relative to untreated patents; and (iii) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease, such as decreasing tumor size and/or incidence of metastasis. Suitable tumor cells include without limitation lymphoma cell, breast cancer cell, melanoma cell, plasmacytoma cell, sarcoma cell, glioma cell, thymoma cell, leukemia cell, prostate cancer cell, colon cancer cell, esophageal cancer cell, lung cancer cell, ovarian cancer cell, cervical cancer cell and hepatoma cell.

In a further aspect, the invention provides methods of treating tumor in a mammal comprising administering to a mammal in need thereof an amount effective to treat the tumor of a composition that comprises a first ligand that is specific for a tumor cell, and a second ligand that is specific for a death receptor on the tumor cell, wherein the first and second ligands are bound to a nucleic acid nanostructure. In certain preferred embodiments, the first ligand is a first aptamer and the second ligand is a second aptamer. All preferred embodiments applicable to the other aspect of the invention with regard to the inventive aptamer-nucleic acid nanostructures also apply to this aspect of the invention.

In certain preferred embodiments, the inventive composition is injected into a subject in conjunction with a pharmaceutical acceptable carrier, diluent or excipient known to one of skill in the art for modifying, maintaining, or preserving, in a manner that does not hinder the activities of the inventive composition described herein, for example, pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobial compounds, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, betacyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; Triton; trimethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See REMINGTON'S PHARMACEUTICAL SCIENCES (18th Ed., A. R. Gennaro, ed., Mack Publishing Company 1990).

As used herein, the term "subject" refers to an animal or a mammal and in particular preferred embodiments, a human, in need of the tumor therapy using the inventive compositions.

The primary vehicle or carrier in a pharmaceutical composition may be either aqueous or non-aqueous in nature. For example, a suitable vehicle or carrier for injection may be physiological saline solution, or artificial cerebrospinal fluid. Optimal pharmaceutical compositions can be determined by a skilled artisan depending upon, for example, the intended route of administration, delivery format, desired dosage and recipient tissue. See, e.g., REMINGTON'S PHARMACEU-TICAL SCIENCES, supra. Such compositions may influence the physical state, stability, and effectiveness of the composition.

The pharmaceutical composition to be used for in vivo administration typically is sterile and pyrogen-free. In certain preferred embodiments, this may be accomplished by filtration through sterile filtration membranes. In certain preferred embodiments, where the composition is lyophilized, sterilization using this method may be conducted either prior to or following lyophilization and reconstitution. In certain preferred embodiments, the composition for parenteral administration may be stored in lyophilized form or in a solution. In certain preferred embodiments, parenteral compositions generally are placed into a container having a sterile access port, for example, an intravenous solution bag or vial having a stopper pierceable by a hypodermic injection needle.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The effective amount of a pharmaceutical composition of the invention to be employed therapeutically will depend, for example, upon the therapeutic context and objectives. One skilled in the art will appreciate that the appropriate dosage levels for treatment, according to certain preferred embodiments, will thus vary depending, in part, upon the molecule delivered, the indication for which the pharmaceutical composition is being used, the route of administration, and the size (body weight, body surface or organ size) and/or condition (the age and general health) of the patient. A clinician can titer the dosage and modify the route of administration to obtain the optimal therapeutic effect. Aptamers delivered at 40-400 µg/kg have been shown to be effective in vivo (Mc-Namara wt al., 2008. *J Clin Invest* 118:376-386).

The dosing frequency will depend upon the pharmacokinetic parameters of an aptamer-nucleic acid nanostructure in the formulation. For example, a clinician administers the composition until a dosage is reached that achieves the desired effect. The composition may therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Administration routes for the pharmaceutical compositions of the invention include topically, orally, through injection by intravenous, intraperitoneal, intracerebral (intra-parenchymal), intracerebroventricular, intramuscular, intraocular, intraarterial, intraportal, subcutaneous, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

One of skill in the art would understand that all embodiments described herein in any aspect of the invention can be applied in any other aspects of the invention.

The Examples, which follow, are illustrative of specific embodiments of the invention, and various uses thereof. They are set forth for explanatory purposes only, and are not to be taken as limiting the invention.

EXAMPLES

Example 1

Selection of Aptamers

Aptamers having desirable binding affinity to a tumor antigen on B leukemia Ramos cells are selected from a random aptamer library. Because the Ramos cells express primarily TRAIL-R1, aptamers that specifically bind to TRAIL-R1 are also selected from the random aptamer library. Specifically, TRAIL-R1-Fc fusion protein (catalog No. D9438, Sigma, St. Louis, Mo.), as well as decoy receptors-Fc fusion proteins (catalog No. 630-TR-100, R & D Systems, Minneapolis, Minn.) are incubated with the aptamer library. Candidate aptamers having binding affinity to the TRAIL-R1-Fc fusion protein but not to the decoy receptor-Fc fusion proteins are identified by capillary electrophoresis. Aptamer-fusion protein complexes are detected by the retardation of migration rate in electrophoresis. Candidate aptamers are amplified by the SELEX procedure as known in the art and described in this application.

Example 2

Construction of Bi-Specific Aptamer-Nucleic Acid Nanostructure for Tumor-Specific Killing Although TRAIL-Rs are primarily expressed in tumor cells, they are also found present in normal cells and have been suggested to account for TRAIL-induced toxicity (Zheng et al., 2004, *J Clin Invest* 113:58-64). To achieve tumor-specific targeting, bi-specific aptamer-nucleic acid nanostructures containing tumor-specific aptamers and death receptor-specific aptamers on a DNA-nanostructure are generated. The aptamer M2 as previously reported that is specific to Ramos cells, and does not bind to T-cell leukemia cells has been reported (Shangguan et al., 2006, *Proc Natl Acad Sci USA* 103:11838-11843) (M2 aptamer: 5'-TAGGCAGTG-GTTTGACGTCCGCATG TTGGGAATAGCCACGCCT-3', SEQ ID NO:42). The tumor-specific aptamers M2 are assembled onto a DNA-nanostructure along with the death-inducible aptamers, in which various configurations will be constructed, in terms of position and copy numbers of aptamers, as well as ratio of the tumor-specific and death receptor-specific aptamers as described throughout this application. The optimal configuration is selected based on their ability to induce tumor-specific apoptosis.

Figure 4:
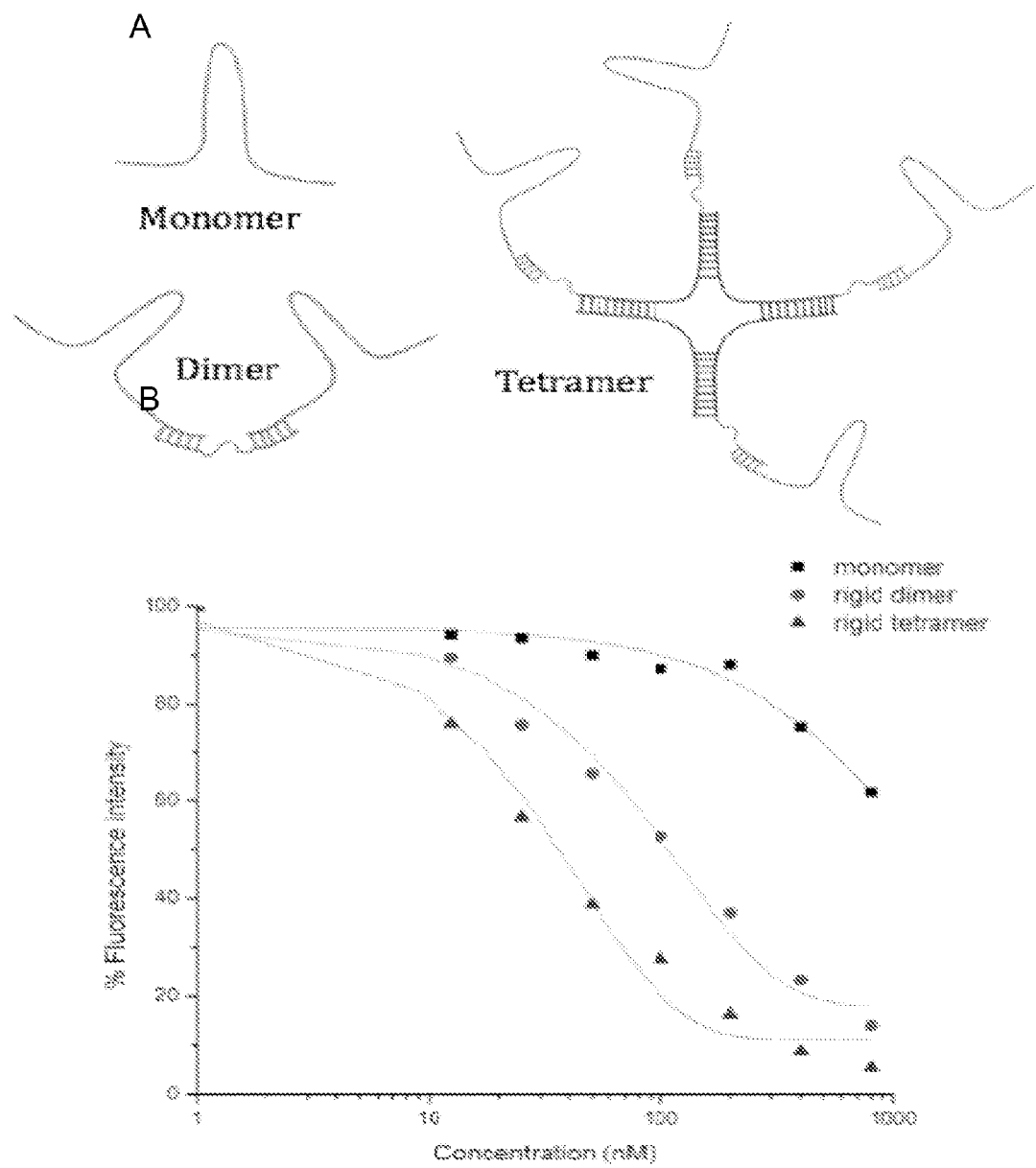
FIG. 4 shows results of competitive inhibition of fluorescently-labeled, monomeric aptamers to B cell leukemia Ramos cells by unlabeled mono- or multi-valent aptamer-nucleic acid nanostructure. A. Illustration of exemplary monomeric, flexible dimeric and flexible tetrameric aptamers specific to a B cell line. B. Fluorescence intensity assessed by flow cytometry (y-axis) of the cells after incubation with labeled monomer in the presence of various concentrations of unlabeled monomeric, rigid dimeric, or rigid tetrameric aptamers at the indicated concentrations (x-axis). Rigid dimeric and tetrameric aptamers differ from their flexible counterparts in that the rigid multimers do not contain dT in the linker oligonucleotide.

Multimerization further improves the binding avidity of aptamers. The bi-specific aptamer nucleic acid nanostructures contain not only multiple copies of aptamers, but also multivalent aptamers. Competitive inhibition assays were performed where Ramos cells were incubated with fluorescence-labeled monomeric aptamers in the presence of different concentrations of non-labeled monomeric, dimeric or tetrameric aptamers. As shown in FIG. 4, the tetramers most efficiently competed with the labeled monomers for binding to Ramos cells.

The multimeric aptamers are used to construct bi-specific aptamer-DNA nanostructures, which contain the Ramos cell-specific aptamers and aptamers specific for TRAIL-R1 arranged at defined position, as illustrated in FIG. 1. These aptamer-DNA nanostructures are tested for their ability to induce apoptosis in Ramos but not in Jurkat cells because the M2 aptamer is specific for Ramos cells. In addition, aptamer-nucleic acid nanostructures containing other Ramos cell-specific aptamers identified by methods described in this application along with TRAIL-R1-aptamers are constructed and tested for targeted induction of apoptosis in tumor cells as described below.

Approximately 200,000 human B cell lymphoma Ramos cells are incubated with multimeric aptamer-DNA nanostructures at various concentrations in 0.5 ml culture medium (RPMI supplemented with 10% FBS and antibiotics) at 37° C. Twenty-four hours after the incubation, cells are stained with 1 µg/ml propidium iodide (PI) and analyzed by flow cytometry, where PI-positive cells indicate dead cells. Anti-DR4 or DR5 antibodies (for example, catalog Nos. ab8414 and ab47179, respectively, AbCam, Cambridge, Mass.), as well as the DNA damaging agent etoposide are included as a positive control for the induction of apoptosis. Cells cultured in the medium only without the aptamer-DNA nanostructures are served as a negative control, reflecting the background number of dead cells in the culture.

Example 3

Aptamers Remained Stable Under Different Conditions

The stability of the dimeric aptamers was tested in this experiment. The dimeric B cell-specific aptamer M1, which consisted of monomeric aptamer M2, was incubated in the culture medium (1 mg/ml BSA in PBS) with or without human B cell lymphoma at different temperatures. After incubation, aptamers were recovered from the cell mixture by spinning down the cells. The supernatants were treated with phenol/chloroform to remove proteins, and the aptamers were precipitated by 95% ethanol. The recovered aptamer DNA was dissolved in $H_2O$ and separated by a native polyacrylamide gel (16%) to check the integrity of the aptamers-nanostructure.

Figure 5:
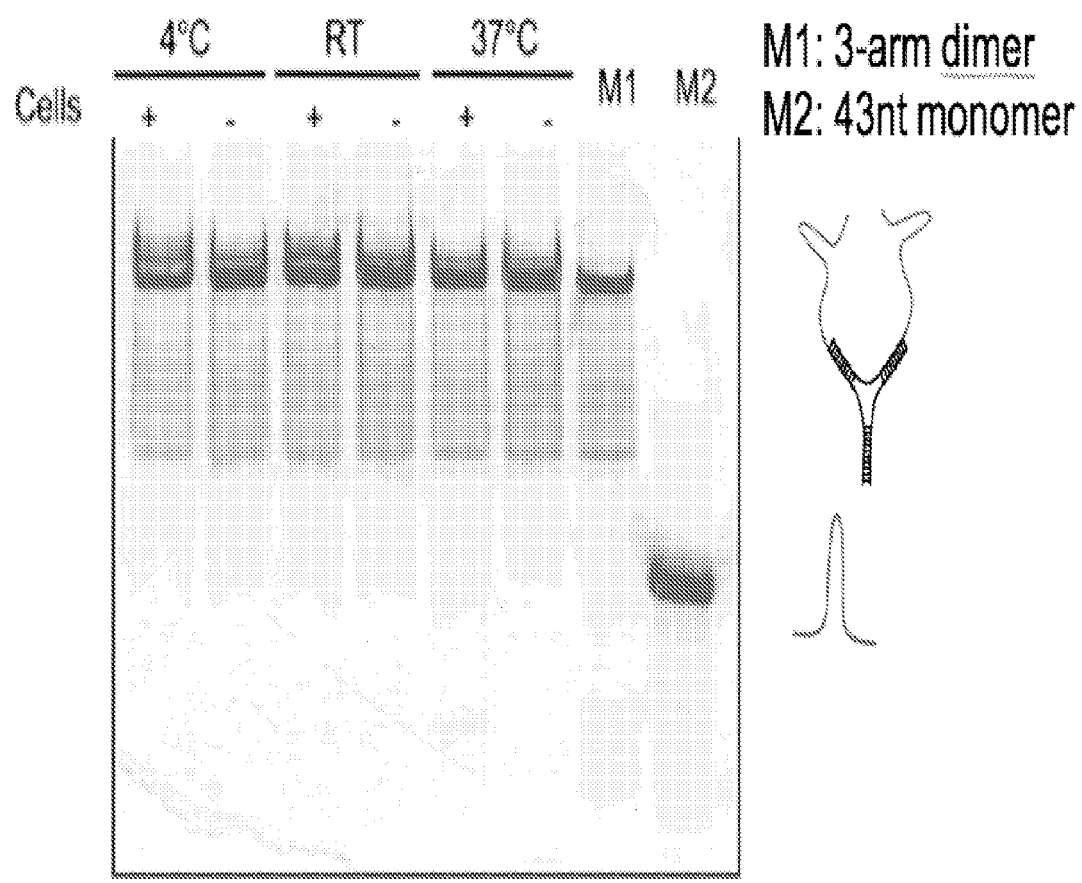
FIG. 5 shows a photograph of image of native gel electrophoresis of M1 dimeric aptamer incubated with or without cells at different temperatures. M1 and M2 are input dimeric and monomeric DNA aptamers, respectively, as illustrated on the right.

As shown in FIG. 5, the integrity and levels of recovered aptamers were comparable under all conditions tested, including incubating with or without cells in the culture medium at 4° C., room temperature, and 37° C. Thus, this multimeric aptamer-DNA nanostructure was relatively stable in cell culture. Chemical modifications are introduced to further enhance the stability of the aptamer-DNA nanostructure. See Keefe et al., 2008, *Curr Opin Chem Biol* 12:448-456.

Example 4

Multi-Functional Aptamer-Nucleic Acid Nanostructure is Constructed for Synergized Tumor Cells Killing In further experiments, factors promoting apoptosis are included into the aptamer-nucleic acid nanostructures to provided synergized tumor cell killing. An NF-κB decoy oligonucleotide comprising the sequence GGATTTCCC-3' that functions as NF-κB inhibitor is incorporated into the aptamer-nucleic acid nanostructures (see FIG. 6). The number and position as well as the ratio of NF-κB decoy oligonucleotides to the aptamer molecules are evaluated during the construction of these multifunctional complexes. The levels of apoptosis induction are compared between these multifunctional aptamer-nucleic acid nanostructures containing NF-κB inhibitor and the bi-specific nanostructures that do not contain an NF-κB inhibitor.

It should be understood that the foregoing disclosure emphasizes certain specific embodiments of the invention and that all modifications or alternatives equivalent thereto are within the spirit and scope of the invention as set forth in the appended claims.

What is claimed is:

1. A composition comprising a first ligand that is specific for binding to a tumor cell, and a second ligand that is specific for binding to a death receptor on the tumor cell, wherein the first and second ligands are bound to a nucleic acid nanostructure, wherein the first ligand is a first aptamer and the second ligand is a second aptamer, and wherein the nucleic acid nanostructure comprises a nucleic acid tile.

2. The composition of claim 1, wherein the first aptamer is specific for binding to a tumor antigen on the surface of the tumor cell.

3. The composition of claim 2, wherein the tumor antigen is CD20.

4. The composition of claim 1, wherein the death receptor is TRAIL Receptor 1 (TRAIL-R1), TRAIL Receptor 2 (TRAIL-R2) or tumor necrosis factor receptor (TNFR).

5. The composition of claim 1, wherein the distance between the first aptamer and the second aptamer on the nucleic acid nano structure is about 10 nm to about 15 nm.

6. The composition of claim 1, wherein the first aptamer comprises a plurality of first aptamers, and the second aptamer comprises a plurality of second aptamers.

7. The composition of claim 6 wherein the plurality of first aptamers is present on the nucleic acid nanostructure at a density of 5-10 aptamers per nucleic acid nanostructure, and the plurality of second aptamers is present on the nucleic acid nanostructure at a density of 5-10 aptamers per nucleic acid nanostructure.

8. The composition of claim 7 wherein the distance between each aptamer of the plurality of first aptamers and the distance between each aptamer of the plurality of second aptamers on the nucleic acid nanostructure is about 5 nm to about 8 nm.

9. The composition of claim 8, wherein the ratio of first aptamers to second aptamers on the nucleic acid nanostructure is 1:1.

10. The composition of claim 1, wherein the first aptamer comprises a dimer, trimer, tetramer, or pentamer of an aptamer that is specific for a tumor cell.

11. The composition of claim 10, wherein the second aptamers comprises a dimer, trimer, tetramer, or pentamer of an aptamer that is specific for binding to the death receptor.

12. The composition of claim 11, wherein the first aptamer comprises a plurality of first aptamers, and the second aptamer comprises a plurality of second aptamers.

13. The composition of claim 12 wherein the plurality of first aptamers is present on the nucleic acid nanostructure at a density of 5-10 aptamers per nucleic acid nanostructure, and the plurality of second aptamers is present on the nucleic acid nanostructure at a density of 5-10 aptamers per nucleic acid nanostructure.

14. The composition of claim 13 wherein the distance between each aptamer of the plurality of first aptamers and the distance between each aptamer of the plurality of second aptamers on the nucleic acid nanostructure is about 10 nm to about 15 nm.

15. The composition of claim 14, wherein the ratio of first aptamers to second aptamers on the nucleic acid nanostructure is 1:1.

16. The composition of claim 6, wherein the first aptamer comprises a plurality of first aptamers that are specific for binding to at least two different tumor antigens on the surface of the tumor cell.

17. The composition of claim 6, wherein the second aptamer comprises a plurality of second aptamers that are specific for binding to at least two different death receptors.

18. The composition of claim 1, further comprising an apoptosis inducer that is bound to the nucleic acid nanostructure.

19. The composition of claim 18, wherein the apoptosis inducer is an NF-KB inhibitor.

20. The composition of claim 19 wherein the NF-KB inhibitor is a decoy oligonucleotide.

21. The composition of claim 1, wherein the nucleic acid nanostructure is between about 10 nm and about 2000 nm in length.

22. The composition of claim 1, wherein the nucleic acid nanostructure comprises a plurality of nucleic acid tiles.

23. The composition of claim 22, wherein the plurality of nucleic acid tiles forms a nucleic acid tiling array.

24. The composition of claim 1, further comprising a pharmaceutically acceptable carrier.

* * * * *